(12) United States Patent
Rempfer et al.

(10) Patent No.: US 9,259,710 B2
(45) Date of Patent: Feb. 16, 2016

(54) SEPARATION MATERIAL COMPRISING SACCHARIDE LIGANDS

(75) Inventors: Martin Rempfer, Gomaringen (DE); Wolfgang Freudemann, Hechingen (DE); Cornelia Winz, Rottenburg-Weiler (DE); Ralf Flieg, Rangendingen (DE); Markus Storr, Filderstadt (DE); Manuela Klotz, Hechingen (DE); Sandra Homeyer, Ofterdingen (DE); Torsten Knoer, Burladingen (DE)

(73) Assignee: Gambro Lunia AB, Lund (SE)

(*) Notice: Subject to any disclaimer, the term of this patent is extended or adjusted under 35 U.S.C. 154(b) by 11 days.

(21) Appl. No.: 14/237,182

(22) PCT Filed: Aug. 7, 2012

(86) PCT No.: PCT/EP2012/065388
§ 371 (c)(1),
(2), (4) Date: Apr. 16, 2014

(87) PCT Pub. No.: WO2013/020964
PCT Pub. Date: Feb. 14, 2013

(65) Prior Publication Data
US 2015/0111194 A1    Apr. 23, 2015

(30) Foreign Application Priority Data
Aug. 8, 2011 (EP) .................................... 11176769

(51) Int. Cl.
*B01J 20/32* (2006.01)
*B01J 20/26* (2006.01)
*B01J 20/289* (2006.01)

(52) U.S. Cl.
CPC .............. *B01J 20/3278* (2013.01); *B01J 20/26* (2013.01); *B01J 20/289* (2013.01); *B01J 20/321* (2013.01); *B01J 20/3212* (2013.01); *B01J 20/3219* (2013.01); *B01J 20/3251* (2013.01); *B01J 20/3255* (2013.01); *B01J 20/3274* (2013.01); *B01J 20/3291* (2013.01); *B01J 2220/80* (2013.01)

(58) Field of Classification Search
CPC ........ B01J 20/26; B01J 20/289; B01J 20/321; B01J 20/3278; B01J 20/3274; B01J 20/3255; B01J 20/3219; B01J 20/3291; B01J 20/3212; B01J 20/3251; B01J 2220/80
See application file for complete search history.

(56) References Cited

U.S. PATENT DOCUMENTS

| 3,947,352 | A | 3/1976 | Cuatrecasas et al. |
| 4,411,832 | A | 10/1983 | Cuatrecasas et al. |
| 5,670,483 | A | 9/1997 | Zhang et al. |
| 5,955,343 | A | 9/1999 | Holmes et al. |
| 6,548,630 | B1 | 4/2003 | Zhang et al. |
| 6,686,457 | B1* | 2/2004 | Nilsson .......................... 536/4.1 |
| 6,800,481 | B1 | 10/2004 | Holmes et al. |
| 7,700,746 | B2 | 4/2010 | Nilsson |
| 2005/0181973 | A1 | 8/2005 | Genove et al. |
| 2007/0296105 | A1 | 12/2007 | Krause et al. |
| 2009/0081701 | A1* | 3/2009 | Cen ............................... 435/7.2 |

FOREIGN PATENT DOCUMENTS

| EP | 0371636 | 6/1990 |
| EP | 0305687 | 4/1992 |
| EP | 0844015 | 10/2003 |
| EP | 1518870 | 3/2005 |
| EP | 1165159 | 3/2008 |
| EP | 1875956 | 3/2010 |
| EP | 1875957 | 3/2010 |
| EP | 2281625 | 2/2011 |
| EP | 2113298 | 4/2013 |
| EP | 2228126 | 4/2013 |
| WO | WO01/60477 | 8/2001 |

OTHER PUBLICATIONS

Bryan, M.C., et al.; Journal of the American Chemical Society, 2004, p. 8640-8641.*
PCT Search Report and Written Opinion for PCT/EP2012/065388, completed Sep. 25, 2012.
PCT Search Report and Written Opinion for PCT/EP2012/065394, completed Sep. 4, 2012.
Lee, Myung-Ryul, et al., "Fabrication of Chemical Microarrays by Efficient Immobilization of Hydrazide-Linked Substances on Epoxide-Coated Glass Surfaces", 2005, Angew. Chem. Int. Ed., No. 44, pp. 2881-2884.
Parthasarathy, N., et al., "Application of Carbohydrate Microarray Technology for the Detection of Burkholderia Pseudomallei, Bacillus Anthracis and Francisella Tularensis Antibodies", 2008, Carbohydrate Research, No. 343, pp. 2783-2788.
Monsigney et al., "Colorimetric Determination of Neutral Sugars by a Resorcinol Acid Micromethod," 1988 Analytical Biochemistry 175, 525-530.
Bryan et al., "Colvalent Display of Oligosaccharide Arrays in Microtiter Plates," 2001 Jour. Am. Chem. Soc. 2000, vol. 126. No. 28, 8640-8641.
Tolborg et al., "Solid-phase oligosaccharide synthesis with tris(alkoxy)benzyl amine (BAL) safety-catch anchoring," Chem. Comm. Chem. Soc. 2000, No. 2, 147-148.

* cited by examiner

*Primary Examiner* — Robert Jones, Jr.
(74) *Attorney, Agent, or Firm* — Barnes & Thornburg LLP

(57) ABSTRACT

A separation material includes a saccharide bound via a linker to a matrix for enabling the separation from a liquid of substances that selectively bind to saccharide moieties. A method for preparing the material, a method for separating from a liquid substances that selective bind to saccharides, and a device including the separation material are also disclosed.

10 Claims, 3 Drawing Sheets

SEPARATION MATERIAL COMPRISING SACCHARIDE LIGANDS

CROSS-REFERENCE TO RELATED APPLICATIONS

Figure 1A:
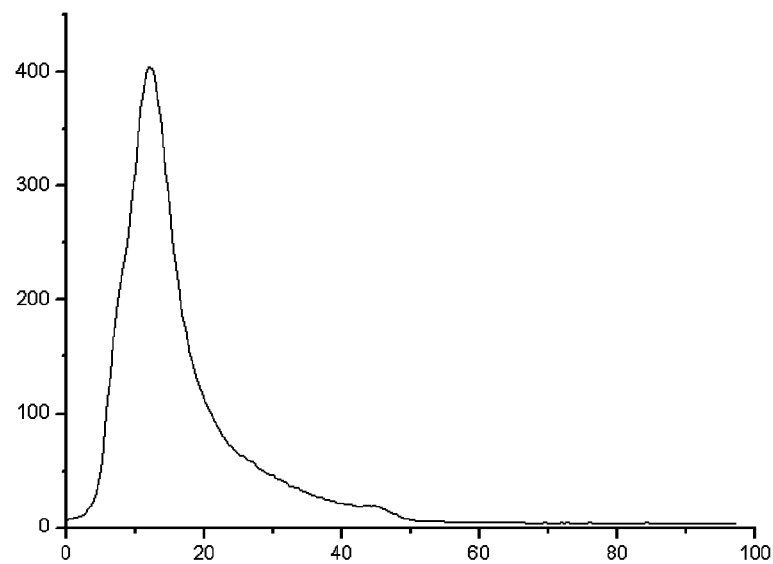

This application is the U.S. national phase of PCT/EP2012/065388 filed Aug. 7, 2012. PCT/EP2012/065388 claims priority to European patent application 11176769.5 filed Aug. 8, 2011. The disclosures of both European patent application 11176769.5 and PCT/EP2012/065388 are hereby incorporated herein by reference.

TECHNICAL FIELD

The present invention relates to a separation material comprising a matrix that is bound via a linker to a saccharide for enabling the separation of substances from a liquid that selectively bind to saccharide moieties. The present invention further relates to a method for preparing said separation material, to a method for separating substances from a liquid that selectively bind to saccharides and to a device comprising said separation material for separating saccharide binding substances from a liquid.

BACKGROUND OF THE INVENTION

EP 1 165 159 B1 is directed to a column for the treatment of whole blood or blood plasma, to a method for extracorporeal removal of blood group A and blood group B antibodies from whole blood or blood plasma, to a saccharide-linker-O-matrix product and to the use thereof in a column during extracorporeal treatments. The saccharide disclosed is a blood group determinant A or a blood determinant B, while the matrix can be a polymeric material or a polysaccharide, especially agarose. The linker is an alkyl that can bear an aromatic moiety, a peptide, a protein or a polysaccharide.

U.S. Pat. No. 7,700,746 B2 discloses a filtration material comprising a saccharide which is coupled to a linker, which in turn is coupled to an agarose matrix, wherein the linker is an alkyldiamine or an anilyl alkyl alcohol derivative.

While these separation materials show good properties in binding and removing e.g. blood antibodies, there is still a desire to provide new materials enabling an enhancement of the performance.

SUMMARY OF THE INVENTION

It is an object of the present invention to provide a new separation material for selectively separating substances from a liquid, preferably whole blood or blood components, such as blood plasma.

In one embodiment of the invention, the material is designed to remove anti-A and/or anti-B antibodies from whole blood or plasma.

According to one aspect of the invention, a separation material comprising a saccharide-linker-matrix is provided. The saccharide is glycosidically coupled to the linker, which is attached to the matrix.

In one embodiment of the invention, the saccharide is a blood group determinant. In another embodiment of the invention, the saccharide is a ligand for blood group antibodies. Such blood group antibodies are anti-A or anti-B antibodies. In yet another embodiment of the invention, the matrix is a synthetic polymeric material, a peptide or a polysaccharide.

According to another aspect of the invention, a method for selectively separating or removing substances from a liquid using a separation material according to the present application is provided. In one embodiment of the invention, the liquid is whole blood or plasma.

According to yet another aspect of the invention, a device for selectively separating, removing or isolating substances from a liquid is provided, comprising a separation material according to the present application. In one embodiment of the invention, the device serves for removing from whole blood or plasma certain blood components. In another embodiment of the invention, such blood components are blood group antibodies.

SHORT DESCRIPTION OF THE FIGURES

Figure 1B:

FIG. 1B shows a two photons excitation microscopy image of a plasma amino functionalized hollow fiber membrane having a wall thickness of 50 μm. Also shown is the relative fluorescence spectrum (FIG. 1A). The amino functions were reacted with 4-fluoro-7-nitrobenzo-2-oxa-1,3-diazole (NBD-F) as fluorophore. The area of the image is 100 μm×50 μm. The x-axis of the spectrum shows the width in μm, the y-axis the relative fluorescence intensity.

Figure 2:
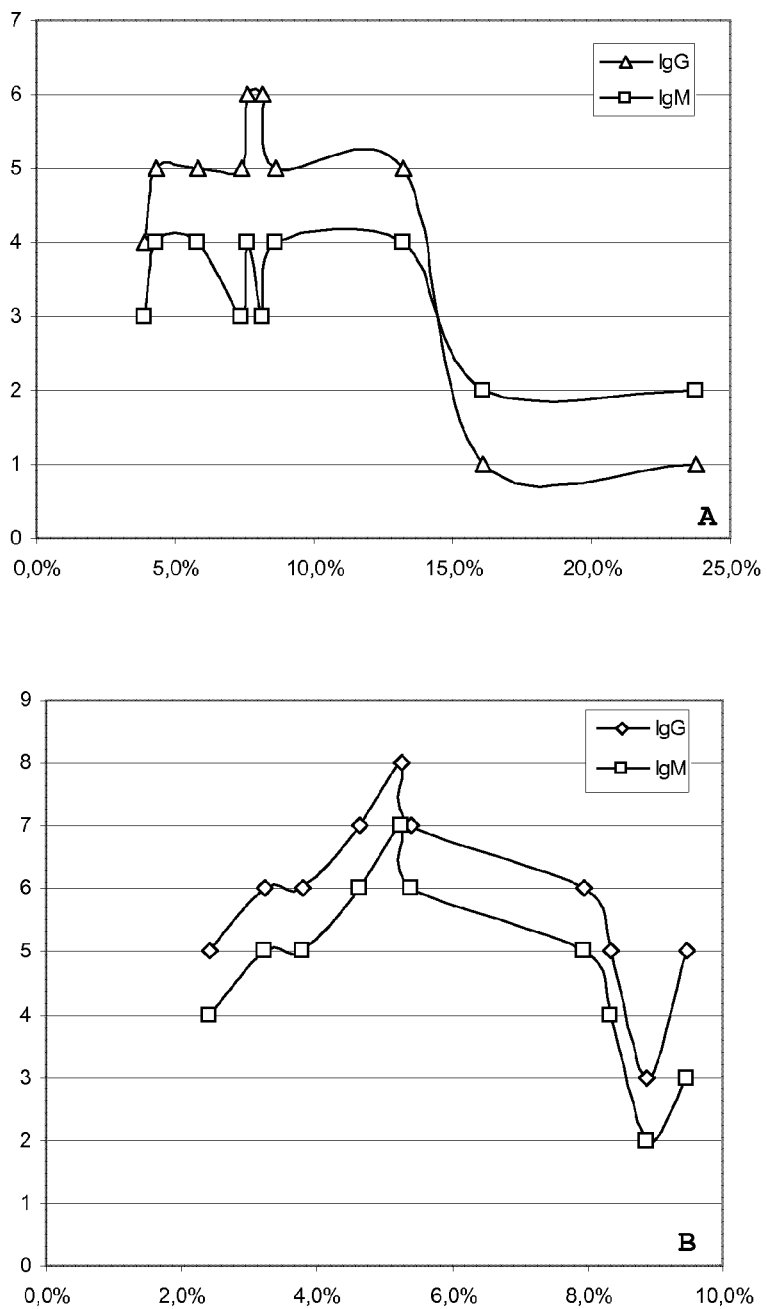

FIG. 2 shows the dependency of the titer reduction (IgG and IgM) on the proportion of saccharide amount (TsB_ANA) and amount of functionalization of the initial matrix with a linker according to formula (II), 6-aminohexanoic acid (see also Example 25). The x-axis shows the proportion of total amount of saccharide (TsB_ANA) present on the matrix in [μmol/g] per total amount of linker (6-AHS) present on the matrix in [mmol/g] in %. FIG. 2A shows the results for a matrix with an average particle size range (diameter) of 100-300 μm (Mitsubishi ReliZyme™ EXE 135). FIG. 2B shows the results for a matrix with an average particle size range (diameter) of 25-90 μm (Mitsubishi ReliZyme™ EXE 148). As can be seen, there is a certain preferred range concerning the amount of functionalization of the matrix with 6-AHS for the matrix used, which cannot be significantly improved by increasing the amount of saccharide immobilized on the material. Accordingly, an optimal functionalization range can be determined for each matrix.

Figure 3:
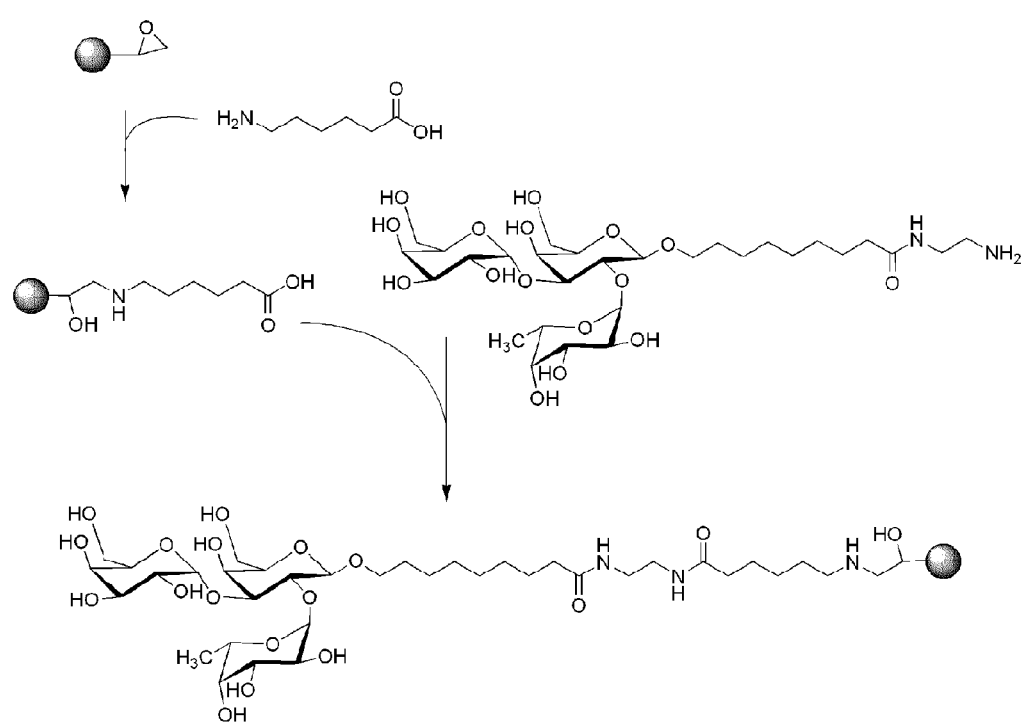

FIG. 3 shows a typical example for the synthesis design for a separation material according to the invention. An oxirane function carrying matrix is coupled to a linker group, 6-aminohexanoic acid. The functionalized matrix is coupled to a functionalized saccharide, TsB_ANA, resulting in the final separating material according to the invention.

DETAILED DESCRIPTION

It is one aspect of the present invention to provide a material comprising a saccharide which is bound via a linking group to a matrix. This saccharide-linker-matrix is represented by general formula (I)

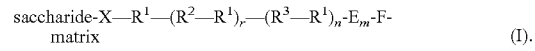

saccharide-X—R$^1$—(R$^2$—R$^1$)$_r$—(R$^3$—R$^1$)$_n$-E$_m$-F-matrix     (I).

The saccharide is linked glycosidically to the adjacent group which links the saccharide to the matrix.

In one embodiment of the invention, r, n and m are 1, respectively. In another embodiment, r and m are 1 and n is 0. In yet another embodiment, r and m are 1 and n is 2. In yet another embodiment, r and m are 1 and n is 3.

The expression "linker", as it is used herein, refers to the portion of formula (I) which is represented by the general formula (II)

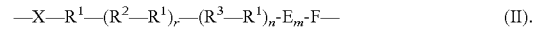

—X—R$^1$—(R$^2$—R$^1$)$_r$—(R$^3$—R$^1$)$_n$-E$_m$-F—     (II).

X represents O, S, CH$_2$ or NR', wherein R' represents H, methyl or a suitable protecting group.

Suitable protecting groups for amines are acetyl (Ac), trifluoroacetyl (TFA), trichloroacetyl, benzoyl (Bz), benzyl (Bn), tert-butyloxycarbonyl (BOC), carbobenzyloxy (Cbz), p-methoxybenzyl carbonyl (Moz), 9-fluorenylmethyloxycarbonyl (FMOC), vinyloxycarbonyl (Voc), allyloxycarbonyl (Alloc), p-methoxybenzyl (PMB), 3,4-dimethoxybenzyl (DMB), p-methoxyphenyl (PMP), triphenylmethyl (Tr), tosyl (Ts) or nosyl (Ns).

$R^1$ represents, independently of one another, straight-chain or branched $C_1$-$C_{10}$ alkyl such as methyl, ethyl, n- or isopropyl, n-, iso-, sec- or tert-butyl, n-pentyl, n-hexyl, n-heptyl, n-octyl, n-nonyl or n-decyl, preferably $C_1$-$C_6$ alkyl, wherein the alkyl group can be unsubstituted, or substituted with at least one suitable substituent, selected from the group of substituents comprising halogen, alkyl, alkoxy, haloalkyl, cyano, nitro, amino, hydroxy, thiol, acylamino, alkoxycarbonylamino, haloalkoxycarbonylamino or alkylsulfonylamino.

In one embodiment of the invention, $R^1$ independently of one another represents straight-chain or branched unsubstituted alkyl of the formula —$(CH_2)_{1-10}$—.

In another embodiment of the invention, the group of substituents of $R^1$ comprises amino, hydroxy, thiol, or chlorine.

In yet another embodiment of the invention, $R^1$ represents independently of one another substituted or unsubstituted methyl, ethyl, 1-propyl, 2-propyl, 1-butyl, 2-butyl, 2-methyl-1-propyl, pentyl, 2-pentyl, 3-pentyl, 2-methyl-1-butyl, 3-methyl-1-butyl, 2-ethyl-1-propyl, hexyl, 2-hexyl, 3-hexyl, 4-methyl-1-pentyl, heptyl, 2-heptyl, octyl, 2-octyl, 2-ethyl-1-hexyl, wherein the substituents are as defined before. In yet another embodiment of the invention, $R^1$ represents independently of one another straight-chain unsubstituted methyl, ethyl, propyl, butyl, pentyl, hexyl, heptyl or octyl.

$R^2$ independently of one another represents —CO—NH—, —NH—CO—, —CO—NH—NH—, —NH—NH—CO—, —CH=N—NH—, —NH—N=CH—, —N=CH—, —CH=N— or triazolyl.

In one embodiment of the invention, $R^2$ independently of one another represents —CO—NH—, —NH—CO—, —CO—NH—NH—, —NH—NH—CO—, —CH=N—NH—, —NH—N=CH—, —N=CH—, or —CH=N—. In one embodiment of the invention, $R^2$ independently of one another represents —CO—NH—, —NH—CO—, —CO—NH—NH—, —NH—NH—CO—, —N=CH—, or —CH=N—. In another embodiment of the invention, $R^2$ independently of one another represents —CO—NH— or —NH—CO—.

$R^3$ independently of one another represents —O—, —S—, —CO—NH—, —NH—CO—, —N=CH— or —CH=N—.

r represents 0 or an integer from 1-10.

In one embodiment of the invention, r is 0 or 1.

n represents 0 or an integer from 1-600.

In one embodiment of the invention, n is 0 or an integer from 1 to 5. In another embodiment of the invention, n is 0. In yet another embodiment of the invention, n represents an integer from 500 to 600.

F represents —NH—, =N—, =CH—, —CO—, —CH$_2$—C(OH)—, —NH—CH$_2$—C(OH)—, —NH—NH—, =N—NH—, —CO—NH—, —NH—CO— or triazolyl.

In one embodiment of the invention, F represents —NH—, —CO— or —CH$_2$—C(OH)—.

m represents 0 or 1.

In one embodiment of the invention, m is 1.

E represents —NH—, —CO—, —O—, —S—, —N=, —CH=, —NH—NH—, —NH—N= or triazolyl.

In one embodiment of the invention, E represents —CO— or —NH—.

The separation material of formula (I) is prepared, for example, by coupling a functionalized matrix and/or a saccharide with a compound of the general formula (III)

wherein $R^1$, $R^3$ and n are as defined before, and $R^{3A}$ represents HOOC—, H$_2$N—, HC≡C—, N$_3$—, NH$_2$—NH— or OH—.

$E^1$ represents —COOH, —CHO, —NH$_2$, —SH, —OH, —N$_3$, —NH—NH$_2$ or —C≡CH.

In one embodiment of the invention $R^{3A}$ represents HOOC— or H$_2$N—, $E^1$ represents —COOH or —NH$_2$, and n represents 0.

In one embodiment of the invention $E^1$ represents —COOH, —CHO, or —NH$_2$. In another embodiment of the invention, $E^1$ represents —NH$_2$ or —COOH.

$R^{3A}$ and $E^1$ may be the same or different.

In one embodiment of the invention, n is 0 and formula (III) becomes general formula (IIIA)

wherein $R^{3A}$, $R^1$ and $E^1$ are as defined before.

In another embodiment of the invention, the compound of formula (IIIA) may be coupled with at least one further compound of formula (IIIA), which may be same or different, before reacting it with the matrix of formula (IV) or the saccharide of formula (V). The resulting compound may also be represented by the general formula (III), wherein $R^{3A}$, $R^1$, $R^3$, n and $E^1$ are as described before. In a specific embodiment of the invention, n is an integer from 2 to 10.

In one embodiment of the invention, the compound of formula (III) is reacted with a matrix of the general formula (IV)

wherein $F^1$ represents H$_2$N—, N$_3$—, HOOC—, OHC—, NH$_2$—NH—, HC≡C— or epoxy.

In one embodiment of the invention, $F^1$ is H$_2$N—, HOOC— or epoxy. In yet another embodiment, $F^1$ is H$_2$N— or epoxy.

The resulting product may then be reacted with a saccharide having the general formula (V)

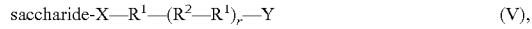

wherein

X, r, $R^1$ and $R^2$ are defined as before, and

Y represents —COOH, —NH$_2$, —CC≡H, —N$_3$, —NH—NH$_2$ or —OH.

In one embodiment of the invention, Y represents —COOH or —NH$_2$.

In another embodiment of the invention, the compound of formula (III) is reacted first with the saccharide of formula (V) and, in a second step, is coupled to the matrix of formula (IV).

In one embodiment of the invention, the compounds of formula (III) are selected from the group of compounds comprising dicarboxylic acids of the general formula HOOC—R—COOH, diamines of the general formula H$_2$N—R—NH$_2$ and amino acids of the general formula H$_2$N—CHR—COOH or H$_2$N—(CH$_2$)$_n$—COOH, wherein n is an integer from 1 to 10.

In another embodiment of the invention, the compound of formula (III) is selected from the group of compounds comprising 2-aminoethanol, 3-aminopropanol, 4-aminobutanol, 5-aminopentanol, 6-aminohexanol, 7-aminoheptanol, 8-aminooctanol, 9-aminononanol, 10-aminodecanol, 1,2-ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 2-aminoethanethiol, 3-aminopropanethiol, 4-aminobutanethiol, 5-aminopentanethiol, 6-aminohexanethiol, 7-aminoheptanethiol, 8-aminooctanethiol, 9-aminononanethiol, 10-aminodecanethiol, 2-hydroxyethanoic acid, 3-hydroxypropanoic acid, 4-hydroxybutanoic acid, 5-hydroxypentanoic acid, 6-hydroxyhexanoic acid, 7-hydroxyheptanoic acid, 8-hydroxynonanoic acid, 9-hydroxydecanoic acid, 2-aminoethanoic acid, 3-aminopropanoic acid, 4-aminobutanoic acid, 5-aminopentanoic acid, 6-aminohexanoic acid, 7-aminoheptanoic acid, 8-aminononanoic acid, 9-aminodecanoic acid, 2-thioethanoic acid, 3-thiopropanoic acid, 4-thiobutanoic acid, 5-thiopentanoic acid, 6-thiohexanoic acid, 7-thioheptanoic acid, 8-thiononanoic acid, 9-thiodecanoic acid, as well as their branched isomers and their unsaturated derivatives.

In yet another embodiment of the invention, the compound of formula (III) is selected from the group of compounds comprising 2-aminoethanoic acid, 3-aminopropanoic acid, 4-aminobutanoic acid, 5-aminopentanoic acid, 6-aminohexanoic acid, 7-aminoheptanoic acid, 8-aminononanoic acid and 9-aminodecanoic acid. In yet another embodiment of the invention, the compound of formula (III) is 6-aminohexanoic acid.

In yet another embodiment of the invention, the compound of formula (III) is selected from the group of compounds comprising 1,2-ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine and 1,10-decylenediamine.

In yet another embodiment of the invention, the compound of formula (III) is selected from the group of compounds comprising propanedioic acid (malonic acid), butanedioic acid (succinic acid), pentanedioic acid (glutaric acid), hexanedioic acid (adipic acid), heptanedioic acid (pimelic acid), octanedioic acid (suberic acid), nonanedioic acid (azelaic acid), decanedioic acid (sebacic acid), glutathione or dicarboxy-PEG (DC-PEG). In one specific embodiment of the invention, the compound of formula (III) is selected from glutaric acid or adipic acid. In another specific embodiment of the invention, the compound of formula (III) is glutathione.

In one embodiment of the invention, the matrix of formula (IV) carries amino functions $F^1$ on its surface. If $E^1$ of the compound of formula (III) is carboxyl, E will be amide in the resulting material of formula (I). Alternatively, the amino function of the matrix may react with a compound of formula (III) wherein $E^1$ is carbonyl and form a matrix of formula (I) wherein E is an imine or a Schiff base.

In another embodiment of the invention, the amino function of the initial matrix is transformed into $F^1$ being an azide function, the azide being suitable for a click chemistry reaction with a terminal alkyne $E^1$ of the compound of formula (III), leading to E being a triazolyl group.

In a further embodiment of invention, $F^1$ of the matrix of formula (IV) represents a carboxyl group which is reacted with an amine function $E^1$ of the compound of formula (III), leading to E being an amide group.

In yet a further embodiment, the matrix of formula (IV) carries alkyne moieties on its surface. The alkyne groups on the matrix surface are transformed into E being triazolyl groups via cycloaddition with an azide group $E^1$ of the compound of formula (III).

In yet a further embodiment, the matrix of formula (IV) carries hydrazine functions $F^1$ on its surface. A hydrazide linkage is then formed by reaction of the hydrazine with the carboxyl function $E^1$ of a compound of formula (III). Alternatively, the hydrazine group can be present as $E^1$ on a compound of formula (III), whereas the matrix carries accessible carboxyl groups on its surface.

In a further embodiment, the matrix of formula (IV) carries hydrazine functions $F^1$ on its surface. A hydrazone linkage is then formed by reaction of the hydrazine with the carbonyl function $E^1$ of a compound of formula (III). Alternatively, the hydrazine group can be present as $E^1$ on a compound of formula (III), whereas the matrix carries accessible carbonyl groups on its surface.

In a yet further embodiment, the matrix of formula (IV) carries an epoxy function $F^1$ on its surface. A secondary amine function is formed by the reaction of the epoxy function on the matrix and a primary amino function $E^1$ of a compound of formula (III).

Alternatively, the epoxy function on the matrix of formula (IV) may be reacted with a thiol function of $E^1$, leading to E being a thioether and F being —$CH_2$—$CH(OH)$—.

TABLE I

Reaction schemes for various combinations of a matrix of formula (VI) and a compound of formula (III).

| | Matrix with functional group | Compound coupled to the matrix | Product |
|---|---|---|---|
| 1 | ●—$NH_2$ | $HO_2C$—◆ | ●—NH—CO—◆ |
| 2 | ●—$NH_2$ | OHC—◆ | ●—N=CH—◆ |
| 3 | ●—$N_3$ | HC≡C—◆ | ●-triazole-◆ |
| 4 | ●—$CO_2H$ | $H_2N$—◆ | ●—CO—NH—◆ |
| 5 | ●—NH—$NH_2$ | $HO_2C$—◆ | ●—NH—NH—CO—◆ |
| 6 | ●—NH—$NH_2$ | OHC—◆ | ●—NH—N=CH—◆ |
| 7 | ●-epoxy | $H_2N$—◆ | ●—C(OH)—$CH_2$—NH—◆ |

The symbol "●" represents the matrix. The compounds which are coupled to the matrix are the compounds of formula (III) or (IIIA) or coupling products of said compounds with a saccharide of formula (V). Accordingly, only $E^1$ is shown, whereas the remaining molecule is represented by the symbol "◆". The reactions shown here depict the various possibilities for forming a linkage between a compound of formula (III) or (IIIA), or a saccharide-bound version thereof.

In one embodiment of the invention, a compound of formula (III) may be used to directly synthesize the saccharide-linker-matrix of formula (I) by coupling it, successively, first to the matrix (IV) and then to the saccharide (V), or vice versa (Table II).

Compounds of the formula (III) may be formed by reacting at least two compounds of formula (IIIA), wherein $R^{3,4}$ and $E^1$ are different and are chosen in a way which allows a reaction between $R^{3,4}$ of one compound of formula (IIIA) with $E^1$ of another compound of formula (IIIA). The compounds of formula (IIIA) may be the same or different.

In one embodiment of the invention, a compound of formula (III) is formed and subsequently coupled to the matrix of formula (IV) and the saccharide of formula (V) via a remaining group $R^{3,4}$ and a remaining group $E^1$, respectively.

In one embodiment of the invention (Table II), a compound of formula (III) is, in a first step, coupled via $R^{3,4}$ to a saccharide of formula (IV) and a second compound of formula (III) is coupled to the matrix via $E^1$ as described before. In a second step, the linker is being formed by coupling the respective products via the remaining terminal functions $R^{3,4}$ and $E^1$. In one specific embodiment of the invention, the compound of formula (III) which is bound to the saccharide may be the same as the compound of formula (III) which is bound to the matrix. In another specific embodiment of the invention, the compound of formula (III) which is bound to the saccharide may be different from the compound of formula (III) which is bound to the matrix.

In yet another embodiment of the invention, a first compound of formula (III) is coupled to the saccharide, followed by reacting the attached compound having a free $E^1$ group to at least one additional compound of formula (III). The resulting molecule is then reacted with the matrix of formula (IV) (Table II). For example, a first compound of formula (III) may be coupled to the saccharide, wherein the resulting compound has, at its free end, an amine function. This amine function can then be reacted with a dicarboxylic acid, followed by attaching the free carboxylic function of the coupled dicarboxylic acid to an amine group of a matrix of formula (IV).

In yet another embodiment of the invention, the compound of formula (III) which has been coupled to the saccharide has a free carboxy group which is then coupled to a second compound of formula (III) which is a diamine, resulting in an elongation of the linker. The remaining free amino group may then be reacted, for example, with a dicarboxylic acid, resulting in a terminal carboxy group which may then be coupled to a matrix with amino groups on its surface. Alternatively, the free amino group may directly be coupled to a matrix of formula (IV) wherein $F^1$ is carboxy or epoxy.

In another embodiment of the present invention, at least two compounds of formula (III) are successively coupled to the matrix of formula (IV), followed by coupling the resulting product to the saccharide (Table II). The at least two compounds of formula (III) may also be coupled to each other in a first step and then linked to the matrix of formula (IV), followed by the coupling of the saccharide of formula (V).

In a yet another embodiment, the product of formula (I) is formed by reacting a compound of formula (III) to a saccha-

TABLE II

Schematic representations of coupling strategies for arriving at the material of formula (I).

(A)

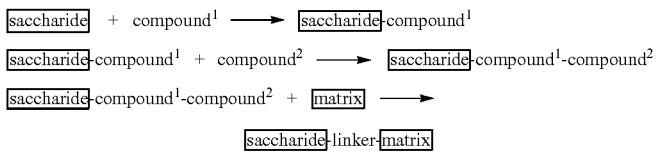

(B)

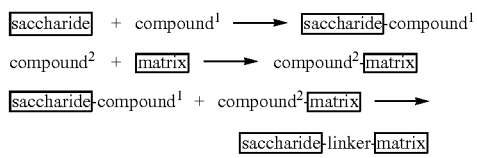

(C)

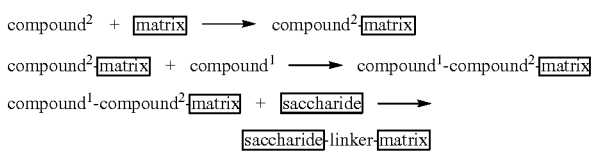

(D)

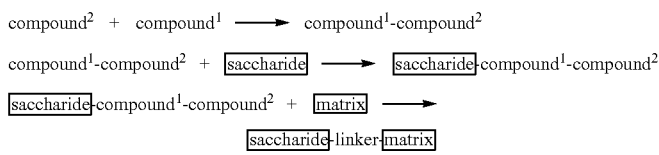

(E)

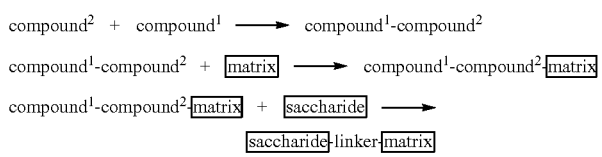

The term "compound1" or "compound2" refers to compounds of formula (III). "compound1" and "compound2" may be the same or different. The term "saccharide" refers to a saccharide compound of formula (V). The term "matrix" refers to a matrix of formula (IV).

ride of formula (V), followed by reacting the resulting molecule to the matrix of formula (IV) or vice versa (Table II).

In another embodiment of the invention, the product of formula (I) is formed by reacting a saccharide of formula (V) to the matrix of formula (IV). The coupling is accomplished by reaction of the functional group Y of the saccharide (V) with the functional group $F^1$ of the matrix (IV).

In one embodiment of the invention, $F^1$ is an amino function and Y a carboxy, leading to an amide as F. In another embodiment, $F^1$ is an azide and Y an alkyne, F being a triazole.

In one embodiment of the invention, a separation material comprising a saccharide-linker-matrix of formula (I) is provided, wherein the saccharide is linked to the matrix via a linker selected from a group of linkers comprising —X(CH$_2$)$_s$—NH—CO—(CH$_2$)$_s$—CONH—, —X(CH$_2$)$_s$—CO—NH—(CH$_2$)$_s$—NH—CO—(CH$_2$)$_s$—CONH—, —X(CH$_2$)$_s$—NH—CO—CH$_2$—(O—C$_2$H$_4$)$_l$—O—CH$_2$—CONH—, —X(CH$_2$)$_s$—CO—NH—(CH$_2$)$_s$—NH—CO—CH$_2$—(O—C$_2$H$_4$)$_l$—O—CH$_2$—CONH—, —X(CH$_2$)$_s$—CONH—, —X(CH$_2$)$_s$—NH—CO—(CH$_2$)$_s$—CO—NH—(CH$_2$)$_s$—NH—CO—(CH$_2$)$_s$—CONH—, —X(CH$_2$)$_s$—CO—NH—(CH$_2$)$_s$—NH—CO—(CH$_2$)$_s$—CO—NH—(CH$_2$)$_s$—NH—CO—(CH$_2$)$_s$—CONH—, —X(CH$_2$)$_s$—CO—NH—(CH$_2$)$_s$—NH—CO—(CH$_2$)$_s$—NH—CH$_2$—CH(OH)—, —X(CH$_2$)$_s$—NH—CO—(CH$_2$)$_s$—NH—CH$_2$—CH(OH)—, —X(CH$_2$)$_s$—CO—NH—(CH$_2$)$_s$—NH—CO—CH(NH$_2$)—(CH$_2$)$_2$—CO—NH—CH(SH)—CO—NH—CH$_2$—CO—NH—CH$_2$—CH(OH)—, wherein
X represents O, N, S or CH$_2$; and
s represents, independently of one another, an integer from 1-10, and
l represents an integer from 1-600.

In one embodiment of the invention, X is O or N. In another embodiment of the invention X is O.

In yet a further embodiment of invention, a separation material of formula (I) is provided, wherein the saccharide is linked to the matrix via the linker

—O—(CH$_2$)$_3$—NH—CO—(CH$_2$)$_3$—CONH—.

In yet a further embodiment of invention, a separation material of formula (I) is provided, wherein the saccharide is linked to the matrix via the linker

—O—(CH$_2$)$_3$—NH—CO—(CH$_2$)$_4$—CONH—.

In yet another embodiment of invention, a separation material of formula (I) is provided, wherein the saccharide is linked to the matrix via the linker

—O—(CH$_2$)$_8$—CO—NH—(CH$_2$)$_2$—NH—CO—(CH$_2$)$_3$—CONH—.

In still another embodiment of invention, a separation material of formula (I) is provided, wherein the saccharide is linked to the matrix via the linker

—O—(CH$_2$)$_8$—CO—NH—(CH$_2$)$_2$—NH—CO—(CH$_2$)$_4$—CONH—.

In a further embodiment of invention, a separation material of formula (I) is provided, wherein the saccharide is linked to the matrix via the linker

—O—(CH$_2$)$_8$—CO—NH—(CH$_2$)$_2$—NH—CO—(CH$_2$)$_5$—NH—CH$_2$—CH(OH)—.

In yet a further embodiment of invention, a separation material of formula (I) is provided, wherein the saccharide is linked to the matrix via the linker

—O—(CH$_2$)$_3$—NH—CO—(CH$_2$)$_5$—NH—CH$_2$—CH(OH)—.

In still another embodiment of the invention, a separation material of formula (I) is provided wherein aminohexanoic acid is coupled to an epoxide functionalized matrix based on a cross-linked copolymer of methacrylate containing oxirane groups, such as, for example, Mitsubishi ReliZyme™ EXE 135 or 148, in aqueous solution at elevated pH, followed by activating the beads with NHS and EDC (1-ethyl-3-(3-dimethylaminopropyl)carbodiimide) in PEG-200, and wherein the activated beads are then reacted with a saccharide of formula (V) having a free amino function, such as, for example, TsB_ANA or TsB_AP.

In another embodiment of the invention, it may prove beneficial to provide a separation material having a certain ratio of a saccharide of formula (V) to a linker of formula (II) which are present on the separation material of formula (I). As can be seen in FIGS. 2A and 2B, the antibody titer reduction (IgG and IgM) has an optimum based on such ratio, which is independent, to a certain degree, of the total amount of saccharide which is bound to the matrix. In tests with 1.5 ml plasma (Example 25) it was shown that for beads such as Mitsubishi ReliZyme™ EXE 135, having a medium average particle size, the optimum is in a range of from 4% to 13% of saccharide per linking group (in µmol/g matrix). For beads such as Mitsubishi ReliZyme™ EXE 148, having a somewhat smaller average particle size, the optimum is in a range of from 4% to 8%.

In one embodiment of the invention, the coupling reaction is carried out by linking a carboxyl with an amine function. The formation of amide bonds as described before can be carried out according to any procedure known to the person skilled in the art. A common method comprises the activation of the carboxylic acid with a carbodiimide, thus facilitating the coupling to an amine. The formation of an amide using a carbodiimide is straightforward, but with several side reactions complicating the subject. The carboxylic acid reacts with the carbodiimide to produce the key intermediate, an O-acylurea, which can be referred to as a carboxylic ester with an activated leaving group. The O-acylurea then reacts with amines to give the desired amide and urea as byproduct. Additives are often added to increase yields and decrease side reactions. These substances can react with the O-acylurea to form an active ester which is less reactive and less in danger of racemization.

Examples of suitable carbodiimides include dicyclohexylcarbodiimide (DCC), diisopropylcarbodiimide (DIC) and 1-ethyl-3-(3-dimethylaminopropyl)carbodiimide (EDC).

Examples of suitable additives include N-hydroxybenzotriazole (HOBt), 1-Hydroxy-7-azabenzotriazole (HOAt), N-hydroxysuccinimide (NHS), and N-hydroxysulfosuccinimide (Sulfo-NHS). An alternative to HOBt and HOAt is ethyl 2-cyano-2-(hydroxyimino)acetate (trade name Oxyma Pure), which is not explosive and has a reactivity of that in between HOBt and HOAt.

Recent reaction schemes totally omit any carbodiimides, introducing the active ester as an uronium or phosphonium salt of a non-nucleophilic anion (tetrafluoroborate or hexafluorophosphate), such as, for example, 2-(1H-benzotriazole-1-yl)-1,1,3,3-tetramethyluronium hexafluorophosphate (HBTU), 2-(7-aza-1H-benzotriazole-1-yl)-1,1,3,3-tetramethyluronium hexafluorophosphate (HATU), 2-(6-Chloro-1H-benzotriazole-1-yl)-1,1,3,3-tetramethylaminium hexafluorophosphate (HCTU), 2-(1H-benzotriazole-1-yl)-1, 1,3,3-tetramethyluronium tetrafluoroborate (TBTU), O-(7-azabenzotriazole-1-yl)-N,N,N',N'-tetramethyluronium tetrafluoroborate (TATU), O—(N-Succinimidyl)-1,1,3,3-tetramethyl uranium tetrafluoroborate (TSTU), benzotriazol-1-yl-oxytripyrrolidinophosphonium hexafluorophosphate (PyBOP). Two uronium types of the coupling additive of Oxyma Pure are also available as COMU and TOTU reagent.

In one embodiment of the invention, the coupling reaction is carried out by triazole formation. The formation of triazoles from an azide and an alkyne, also known as the alkyne azide Huisgen cycloaddition, is carried out as a 1,3-cycloaddition.

A notable variant of the Huisgen 1,3-dipolar cycloaddition is the copper(I) catalyzed variant, in which organic azides and terminal alkynes are united to afford 1,4-regioisomers of 1,2,3-triazoles as sole products. This reaction is termed the copper(I)-catalyzed Azide-Alkyne Cycloaddition (CuAAC). While the reaction can be performed using commercial sources of copper(I) such as cuprous bromide or iodide, the reaction works much better using a mixture of copper(II) (e.g. copper(II) sulfate) and a reducing agent (e.g. sodium ascorbate) to produce Cu(I) in situ. As Cu(I) is unstable in aqueous solvents, stabilizing ligands are effective for improving the reaction outcome, especially if tris-(benzyltriazolylmethyl) amine (TBTA) is used. The reaction can be run in a variety of solvents and mixtures of water and a variety of (partially) miscible organic solvents including alcohols, DMSO, DMF, tBuOH, dioxane, acetone and mixtures thereof.

Further, the reaction can be catalyzed by ruthenium instead of copper. The ruthenium-catalyzed 1,3-dipolar azide-alkyne cycloaddition (RuAAC) gives 1,5-triazoles. Unlike CuAAC in which only terminal alkynes react, in RuAAC both, terminal and internal alkynes, can participate in the reaction.

The azide functional group can be obtained according to standard procedures. For example, the azide functional group can be obtained by reacting an amine function with an azo-transfer compound, such as, for example, trifluoromethanesulfonyl azide or imidazole-1-sulfonyl azide. Alternatively, the azide can be formed by the reaction of an alkyl or benzyl chloride, bromide or tosylate with sodium azide in aqueous solution and by applying microwaves.

Alkynes can be obtained according to standard procedures. Specialty alkynes are prepared by dehydrohalogenation of vicinal alkyl dihalides or vinyl halides. Metal acetylides can be coupled with primary alkyl halides. Via the Fritsch-Buttenberg-Wiechell rearrangement, alkynes are prepared from vinyl bromides. Alkynes can be prepared from aldehydes using the Corey-Fuchs reaction and from aldehydes or ketones by the Seyferth-Gilbert homologation. In the alkyne zipper reaction, terminal alkynes are generated from internal alkynes by treatment with a strong base.

In one embodiment of the invention, the reaction solvent for each reaction step is a single solvent or a mixture of two or more solvents selected from the group comprising water, alcohols, DMSO, DMF, tBuOH, acetone, 1,4-dioxane, methanol, PEG-200 or mixtures thereof.

In one embodiment of the invention, the coupling reaction of a linker compound of formula (III) with a matrix of formula (IV) is done in aqueous solution, preferably at a high pH of about 10 to 13. In yet another embodiment of the invention, the said coupling of a compound of formula (III) with a matrix of formula (IV) is done in borate-KCl buffer.

In one embodiment of the invention, the coupling of a saccharide of formula (V) to a compound of formula (III), which may be in turn be coupled to a matrix of formula (IV), is done in methanol or PEG-200. In another embodiment, said coupling reaction is done in PEG-200.

The term "saccharide" as used in the present invention as such or within formula (V) refers to monosaccharides, disaccharides, oligosaccharides, or polysaccharides. In the context of the present invention, the term may further be defined as a carbohydrate containing molecule or derivative thereof that has biological or any other sort of affinity to another molecule, protein or cell. In one embodiment of the invention, the term "saccharide" refers to a disaccharide, trisaccharide, tetrasaccharide or pentasaccharide.

Saccharides according to the invention may also comprise saccharides which are otherwise linked to proteins in glycoproteins, to lipids in glycolipids. Further, the saccharides according to the invention may have been produced by enzymatic synthesis, by chemical synthesis, recombinant techniques, isolation from natural sources or by a combination of these methods.

In one embodiment of the invention, the saccharide may be a monosaccharide such as, for example, arabinose, lyxose, ribose, ribulose, xylose, xylulose, allose, altrose, glucose, Mannose, gulose, idose, galactose, talose, psicose, fructose, sorbose, tagatose, their respective uronic acids, N-acetylgalactosamine, N-acetylglucosamine, fucose, fuculose, deoxyribose, rhamnose or combinations or modified versions thereof. Modifications may be present on one or more of the saccharides' hydroxyl groups or n-acetyl groups. Further, the di-, tri-, tetra- and pentasaccharides as well as higher oligosaccharides may be formed by a combination of the above listed monosaccharides, wherein the saccharide—which is glycosidically coupled to the linker—has a α- or β-configuration to the linker moiety.

In another embodiment of the invention, the term "saccharide" as used herein alone or within formula (V) is a disaccharide such as, for example, sucrose, lactulose, lactose, maltose, trehalose, isomaltose, or cellobiose.

In yet another embodiment of the invention, the term "saccharide" as used herein alone or within formula (V) is a trisaccharide. Trisaccharides are oligosaccharides consisting of three monosaccharides which are connected by two glycosidic bonds. Analogous to disaccharides, each glycosidic bond can be formed between any hydroxyl group of the underlying monosaccharides. Different bond combinations (regiochemistry) and stereochemistry (alpha- or beta-) are possible, also between the same monosaccharide moieties, which results in triaccharides that are diastereoisomers with different chemical and physical properties.

In one embodiment of the invention, the saccharide is a Galα1-3Gal type of saccharide. In a specific embodiment of the invention, the saccharide is a blood group determinant.

Examples for such saccharides are Galα1-3Gal types of saccharides, comprising, inter alia, blood group determinants A (α-L-Fuc-(1→2)-[α-D-GalNAc-(1→3)]-D-Gal) and B (α-1-Fuc-(1→2)-[α-D-Gal-(1→3)]-D-Gal). These types of saccharides can be employed for binding the respective blood group antibodies, for example before or after transplantation, thus reducing the antibody concentration in the patient's blood or plasma, or for isolating said antibodies from blood.

In a further embodiment of the invention, the term "saccharide" as such or within formula (V) means carbohydrate structures which are specific for toxins, viruses, bacteria and/or cells and may be used for the preparation of separation material for the removal or isolation of any such materials. Such saccharides specific for pathogens, toxins, viruses, bacteria and cells have been described before in literature and can be equally effectively coupled to a matrix according to what is described in the present application. The separation material may then be used to purify, isolate or eliminate proteins, peptides, toxins, viruses, cells and/or bacteria from whole blood, plasma, culture media, food products, water or other materials.

In another embodiment of the invention, a saccharide-linker-matrix of formula (I) comprises carbohydrate structures which are derived from cell surface glycolipids and glycoproteins, generally referred to as tumor or cancer-antigens, may be produced according to the present invention. Such antigens may be recognized by antibodies, for example in connection with prostate-, breast-, intestine- or skin-cancer. Such material may then be used, for example, for isolating such tumor antigen binding antibodies from whole blood, blood plasma, from cell culture media or any other medium the antibodies need to be isolated from. After elution from the separation material, the antibodies can be used for treating said cancer diseases, for example in immunotherapy treatment of cancer.

All suitable matrix materials can be applied for producing the saccharide-linker-matrix of formula (I) according to the present invention. The term "matrix" as used herein in general or within formula (IV) may represent a synthetic polymer, a peptide or a polysaccharide.

In one embodiment of the invention, the term "matrix" represents a polysaccharide. Suitable polysaccharides are, for example, cellulose, nitrocellulose, chitosan, collagen, starch and cross-linked polysaccharide gels such as agarose, Sephadex or Sepharose. Methods for preparing derivatives of polysaccharide matrices have long been known and are, for example, described in U.S. Pat. No. 4,411,832 or U.S. Pat. No. 3,947,352.

In another embodiment of the invention, the term "matrix" represents a peptide matrix, wherein the functionality $F^1$ of formula (IV) may be an integral part of such peptide matrices. Peptide matrices may be generated by the ability of certain peptides to self assemble into macroscopic membranes useful, for example, for in vitro culturing of cells and biomaterial applications. Examples for such peptide matrices are described, for example in U.S. Pat. Nos. 5,670,483, 5,955,343, 6,548,630 and 6,800,481, which relate to amphiphilic peptides having alternating hydrophobic and hydrophilic residues, and their resultant macroscopic membranes. US 2005/0181973 also discloses a self-assembling peptide which may form into a macroscopic membrane.

Synthetic polymeric matrices comprise hydrophilic and hydrophobic synthetic polymers and combinations thereof. The polymers may be selected from the group comprising polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers or any of these polymers modified by introduction of functional groups.

In one embodiment of the invention, the synthetic matrix comprises polymers selected from polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyurethane (PU), polyethylene glycol (PEG), polyvinylpyrrolidone (PVP), polysulfone (PS), polyethersulfone (PES), polyarylethersulfone (PAES) or ethylene vinyl acetate (EVA) and combinations thereof.

In another embodiment of the invention, the synthetic matrix comprises polymers selected from polyacrylate, poly(methyl methacrylate) (PMMA) or polyglycidyl methacrylate (PGMA).

In yet another embodiment of the invention, the synthetic matrix comprises polymers selected from polyvinylpyrrolidone (PVP), polysulfone (PS), polyethersulfone (PES), polyarylethersulfone (PAES) and combinations thereof.

According to one aspect of the present invention, the synthetic material of the matrix per se carries specific functional groups $F^1$ which are needed for coupling a molecule of formula (III) thereto. For example, many functionalized beads are commercially available and known to a person with skill in the art.

In another embodiment, the polymer material lacks suitable functional groups for the coupling of a molecule to the matrix. This is especially true for flat sheet or hollow fiber membranes. In such cases a polymer functionalization step is needed. For example, a synthetic material made of an alkane chain like, e.g., polyethylene, does not comprise suitable functional groups for coupling a molecule thereto. Therefore, suitable functional groups have to be introduced chemically after polymer synthesis. A possibility for modifying a polymer is the known method of plasma functionalization which allows, by selection of suitable gas plasma, to introduce functional groups into polymers. This method comprises, for example, the use of ammonia plasma, wherein amino functions are formed on the surface of the treated polymer. Hence, treatment of e.g. polyethylene with ammonia plasma leads to a polyethylene matrix bearing a certain amount of amino functions. These amino groups may afterwards be reacted with a suitable functional group of the linker, e.g. a carboxyl group. Alternatively, the matrix polymer can be functionalized by plasma activation to obtain carboxylic groups.

A method for functionalizing a semipermeable hollow fiber membrane in a continuous manner is described, for example, in US 2007/0296105 A1, incorporated herein by reference. The semipermeable hollow fiber membrane is fed through a vacuum system comprising a first vacuum sealed chamber having a pressure of at most 300 mbar, a vacuum sealed plasma ignition chamber having a pressure of at most 0.05 mbar before the introduction of a precursor gas, and a last vacuum sealed chamber having a pressure of at most 300 mbar, and any further vacuum sealed chamber located between any of said chambers, all chambers being consecutively connected in series. When the semipermeable hollow fiber membrane substrate reaches the vacuum sealed plasma ignition chamber, in which a precursor gas containing functional groups has been introduced and has displaced any residual air present therein, the semipermeable hollow fiber membrane substrate is subjected to a plasma ignition, wherein said functional groups in the precursor gas are regioselectively and homogeneously bound to the filtrate side, i.e. the outer membrane layer, and at least to a portion of the pore surface of the semipermeable hollow fiber membrane substrate.

In said method the functional groups comprised introduced by the precursor gas may be amino, carboxyl, aldehyde, ester, epoxy, hydroxyl or sulphonic acids groups.

The precursor gas may be diaminocyclohexane (DACH), diethylenetriamine (DETA) or ammonia. Eventually, a carrier gas like helium, nitrogen, argon, hydrogen or mixtures thereof, is mixed with the precursor gas before or in connection with the addition thereof into the plasma ignition chamber.

In said method the pressure in the vacuum sealed chambers is 5-300 mbar, preferably 0.03-5 mbar, and the pressure in the vacuum sealed plasma ignition chamber is 0.0001-0.05 mbar before the introduction of the precursor gas. After the introduction of the precursor gas the pressure in the vacuum sealed plasma ignition chamber is 0.005-10 mbar, preferably 1.3 mbar.

In one embodiment of said method the ignition frequency during the plasma ignition is 1 kHz-13.56 MHz or multiples of 13.56 MHz or microwave frequency. The power is 50-140 W and the voltage of the electrodes is 50-500 V.

This method allows a density of 10-20 µmol amino functions per g of a hollow fiber membrane.

In another embodiment of the invention, a polymer, e.g. in the form of beads, bearing epoxide groups is treated with ammonia to obtain amino functions for coupling a linker to said polymer matrix. In yet a further embodiment of the invention, a polymer bearing epoxide groups is directly coupled to the linker, which bears at least one nucleophilic functional group, such as azide or amino moieties.

The matrix of formula (IV) may be used in form of beads, flat sheet membranes, hollow fiber membranes, or a combination of different geometries in one device.

Suitable beads are, for example, commercially available resins known to a person with skill in the art. In one embodiment of the invention, Tosoh Toyopearl® AF Amino or Epoxy 650-M can be used. Toyopearl® is a methacrylic polymer incorporating high mechanical and chemical stability. Toyopearl® AF-Epoxy 650-M is an activated support resin for affinity chromatography and has an epoxide functionalization of 800 µmol/g. The product is prepared by a high density epoxy functionalization of Toyopearl® HW-65. This material is especially useful when low molecular weight species are to be coupled to the matrix. The particle size distribution is between 40 and 90 µm. Another suitable matrix is Toyopearl® AF-Amino 650-M which is a reactive support resin for affinity chromatography and has 100 µmol/mL amino functions. The product is prepared by introducing amino groups onto Toyopearl® HW-65. Aminoactivated material is able to immobilize ligands with carboxyl or formyl groups. Another commercially available matrix is Toyopearl® AF-Carboxy 650 M having 100 µmol/mL carboxylic functions.

Another commercially available matrix material is ChiralVision Immobead™ 350. This bead is a crosslinked copolymer of methacrylate carrying 100 µmol/g oxirane groups that is suitable for the covalent immobilization of a variety of enzymes. The porous beads are especially designed to have a low diffusion limitation that allows for the immobilization of enzymes with high specific activities. The particle size distribution is between 300 and 700 µm.

A further commercially available matrix material is Mitsubishi ReliZyme™ EXE 135. The matrix is a crosslinked copolymer of methacrylate containing 166 µmol/g oxirane groups. The median pore diameter is between 40 and 60 nm, while the particle size range may be 100-300 µm, on average about 210 µm, or, alternatively, 200-500 µm, depending on the product. In one embodiment of the invention, the matrix used has an average particle size range of 100-300 µm. Another commercially available matrix material is Mitsubishi ReliZyme™ EXE 148, which corresponds to ReliZyme™ EXE 135 but is smaller in size. The average particle size of ReliZyme™ EXE 148 is about 60 µm. In one aspect of the present invention, the average size of the matrix particles is in the range of from 50 µm to about 200 µm.

According to one aspect of the invention, the saccharides of formula (V) are immobilized via the linker of formula (II) on the outer surface of plasma separation membranes. Membranes suitable for plasma separation are known in the art and have been described, for example, in EP 1 875 956 A1 or EP 1 875 957 A1, all incorporated herein by reference. A plasma separation membrane which may be effectively used for preparing a product according to the present invention, is an asymmetric plasma separation membrane which exhibits high permeability for the whole spectrum of plasma proteins and lipoproteins, reflected by a high sieving coefficient of >0.90. In plasma separation it is desired to have the total plasma protein in the separated plasma fraction, whereas the larger corpuscular components of the blood, like blood cells and cell debris, are retained by the membrane. Further, such a plasma separation membrane should exhibit a high surface porosity and total porosity of the membrane to achieve high filtration performance. It should also be characterized by a hydrophilic, spontaneously wettable membrane structure, low fouling properties for long term stable filtration, and low protein adsorption. Such a plasma separation membrane preferably has smooth surfaces in contact with blood, thus avoiding or minimizing haemolysis during blood processing. The membrane should show constant sieving properties and filtration behavior over the whole treatment period. It should further exhibit high biocompatibility, low or no complement activation and low thrombogenicity.

Further, the hollow fiber membrane preferably has an inner diameter in the range of 100 to 500 µm. Lower inner diameters are disadvantageous because they result in too high wall shear rates and increased pressure drop in the fiber. On the other hand, if the inner diameters are too high, this would result in too low shear rates which in crease the risk of haemolysis at low transmembrane pressures. The plasma separation membrane which can advantageously be used for the present invention has a wall thickness in the range of 20 to 150 µm. Lower wall thicknesses are disadvantageous due to reduced mechanical properties of the fiber during production and during its use in the plasma separation module itself. Higher wall thicknesses are disadvantageous because they require increased time intervals to perform the phase inversion process resulting in instable process conditions and an instable membrane. Further, the membrane should have a pore diameter on the selective separation layer in the range of 0.1 to 1 µm. Lower average pore diameters are disadvantageous due to incomplete passage of total plasma proteins through the porous structure.

In another embodiment of the invention, the hollow fiber membrane which may serve as a matrix for coupling saccharides thereto is a membrane for haemodialysis, haemofiltration or haemodiafiltration applications as known in the art. Hollow fiber membranes which may serve as a matrix in the present invention are described in EP 2 113 298 A1, EP 2 281

625 A1 or EP 2 228 126 A1, all incorporated herein by reference. In one embodiment of the invention, the membrane is based on polysulfone or polyethersulfone and a blend thereof with low and/or high molecular weight polyvinylpyrrolidone. In one embodiment thereof, a polyvinylpyrrolidone may be used which consists of a low molecular weight component having a molecular weight of below 100 kDa and a high molecular weight component having a molecular weight of 100 kDa or more.

In one embodiment of the invention, the inner layer or lumen of a plasma or ultrafiltration hollow fiber membrane matrix according to the invention, which generally is the blood contacting layer, is not functionalized with a saccharide according to the invention. The saccharide is coupled via a linker to the outer layer of the hollow fibers, and optionally also to at least a portion of the layer connecting the inner layer with the outer layer, i.e. the pores of the membrane. Accordingly, the functionalization with saccharides is present only on the outer filtrate layer and optionally on at least a portion of the pore surface structures connecting the outer and inner layer of the membrane. Such configuration can be applied, for example, for the removal of blood groups antibodies from whole blood, wherein only blood plasma is able to pass from the inner layer to the outer layer, while blood proteins remain on the lumen side of the membrane. As blood plasma diffuses or convects to the outer layer, the antibodies contained in it are bound by the specific matrix supported antigen.

In blood purification applications, activated sites or ligands present on the membrane may activate certain blood constituents, e.g. thrombocytes. Other blood constituents, e.g. leucocytes, red blood cells and proteins, may to some extent be adhered to such ligands or activated sites on the blood side of the membrane. These undesired reactions are significantly reduced or avoided, as thrombocytes, leucocytes, red blood cells and proteins do not come in contact with the activated sites on the membrane, if functionalized membranes according to the invention are used.

Another aspect of the invention is a diffusion and/or separation and/or filtration device comprising a membrane which is functionalized according to the invention. Examples of such devices are dialyzers, hemofilters, and ultrafilters. Such devices generally consist of a housing comprising a tubular section with end caps. A bundle of hollow fiber membranes is usually arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2, all incorporated herein by reference.

In another embodiment of invention, the separation material comprises functionalized beads. The beads may be packed in a column consisting of a housing comprising a tubular section with end caps.

Another aspect of the invention is the use of the separation material of the invention to selectively remove substances from a liquid by selective reaction of these substances with the saccharide moiety of the separation material.

In one embodiment, the separation material of the present invention is used for extra-corporeal removal of blood group A and/or blood group B antibodies from blood, blood plasma or any other blood product. The separation material may be used in the course of different types of organ transplantations as a part of the treatment of the recipient before, during, and eventually after the transplantation. The removal of blood group A and/or blood group B antibodies is needed to minimize the problem of blood group incompatibility between donor and recipient. Either whole blood or blood plasma of the patient who is awaiting, undergoing or has gone through a transplantation procedure may be passed trough the separation material. The separation material may also be used for blood group compatible transplantations, wherein problems in connection with donor and recipient of the same blood group, but of different blood group subgroups are addressed.

In a further embodiment, the separation material is used for purifying, isolating or eliminating glycoproteins, glycopeptides, viruses and/or bacteria in whole or in part from whole blood, plasma, blood products, cell culture media, food products, water or other materials. The expression "blood products" as used herein refers to any component of the blood which is collected from a donor for use in a blood transfusion. Most blood products consist of specific processed components such as red blood cells, blood plasma, or platelets. Further specific examples comprise, for example, cryoprecipitate, PF24, fresh frozen plasma or cryosupernatant.

In another embodiment of the invention, the separation material is used for isolating antibodies from whole blood or blood plasma, wherein said antibodies bind to tumor- or cancer-antigens, for example in connection with prostate-, breast-, intestine- or skin-cancer. After elution from the separation material, the antibodies may be used for treating said cancer diseases, for example by producing pharmaceutically active reagents. The separation material may also be used for removing an excess of antibodies from whole blood or blood plasma during immunotherapy of cancer.

In one embodiment, the separation material of the invention is used in plasmapheresis type applications. In a further embodiment of the invention, the separation material is used in hemodialysis, hemodiafiltration or hemofiltration type applications. The separation material of the invention can be used for these purposes instead of conventional membranes, but in a similar manner. The person skilled in the art will easily derive the necessary modus operandi.

Another aspect of the invention is the use of the separation material of the invention in bioprocessing applications, plasma fractionation and the preparation of protein solutions. The membrane of the invention can be used for these purposes instead of membranes conventionally used for these purposes. The person skilled in the art will easily derive a suitable modus operandi for the intended application.

It will be understood that the features mentioned above and those described hereinafter can be used not only in the combination specified but also in other combinations or on their own, without departing from the scope of the present invention.

The present invention will now be described in more detail in the examples below. The examples are not intended to limit the scope of the present invention, but are merely an illustration of particular embodiments of the invention.

EXAMPLES

Example 1

Reaction of an Epoxy-Functionalized Matrix with Glutaric Acid and Coupling of a Blood Group B Trisaccharide

The separation material of the present invention is produced by reaction of an epoxy resin according to formula (IV) with glutaric acid according to formula (III) and a blood group B trisaccharide derivative ("TsB_AP") according to formula (V). Different commercially available beads bearing epoxy functions bay be used in the process of preparing the separating material, specifically Tosoh Toyopearls® AF-Epoxy 650-M, ChiralVision Immobead™-350 or Mitsubishi ReliZyme™ EXE 135.

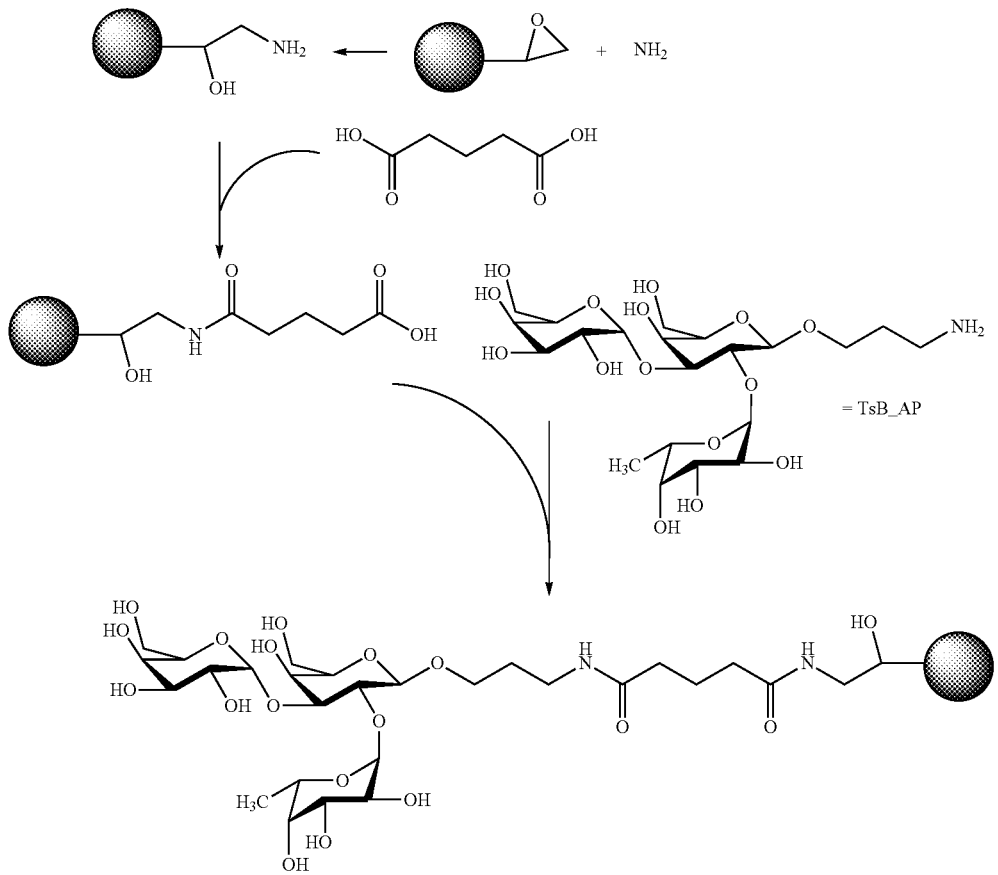

In a first reaction step, the epoxy resin is reacted with ammonia to obtain the respective β-amino alcohol, as the epoxy function is unreactive towards carboxylic acids.

In the next step, amide formation is carried out. The carboxyl groups of glutaric acid are activated for example by the water soluble carbodiimide 1-ethyl-3-(3-dimethylaminopropyl)-carbodiimide (EDC) which forms active O-acylurea intermediates. After initial activation by EDC, the carboxyl groups will react with N-hydroxy-succinimide (NHS) to form an active ester, which couples with the primary amino groups on the surface of the substrate.

In the last step, a saccharide moiety bearing a free amino function is coupled to the free carboxyl function of glutaric acid coupled to the matrix. A commercially available aminopropyl derivative of blood group B determinant trisaccharide TsB_AP (Dextra Science and Technology Centre, Earley Gate Whiteknights Road, Reading, United Kingdom) is attacked to the matrix. The amide formation is accomplished as described for the first step.

Example 2

Reaction of an Amino-Functionalized Matrix with Adipic Acid and Coupling of a Blood Group B Trisaccharide

The separating material of the present invention is produced by using a matrix having free primary amino functions. Hence, the amino functions can be directly coupled to a dicarboxylic acid, such as adipic acid, without previous treatment. As matrix bearing primary amino functions, commercially available beads Tosoh Toyopearls® AF-Amino 650-M are used. Alternatively, a hollow fiber membrane can be functionalized with amino functions by ammonia plasma treatment.

In the first reaction step, coupling of adipic acid as a dicarboxylic acid is performed as described above in Example 1. In the next step, a saccharide of formula (V) having a free amino function is coupled to the remaining carboxyl function of the adipic acid. The commercially available N-(2-aminoethyl) nonane-1-amide derivative of the blood group B determinant trisaccharide is used here ("TsB_ANA", Carbohydrate Synthesis Ltd, North Culham Estate, Culham Science Centre, Abingdon, Oxford, UK) was applied. The amide formation is accomplished as described in the first step.

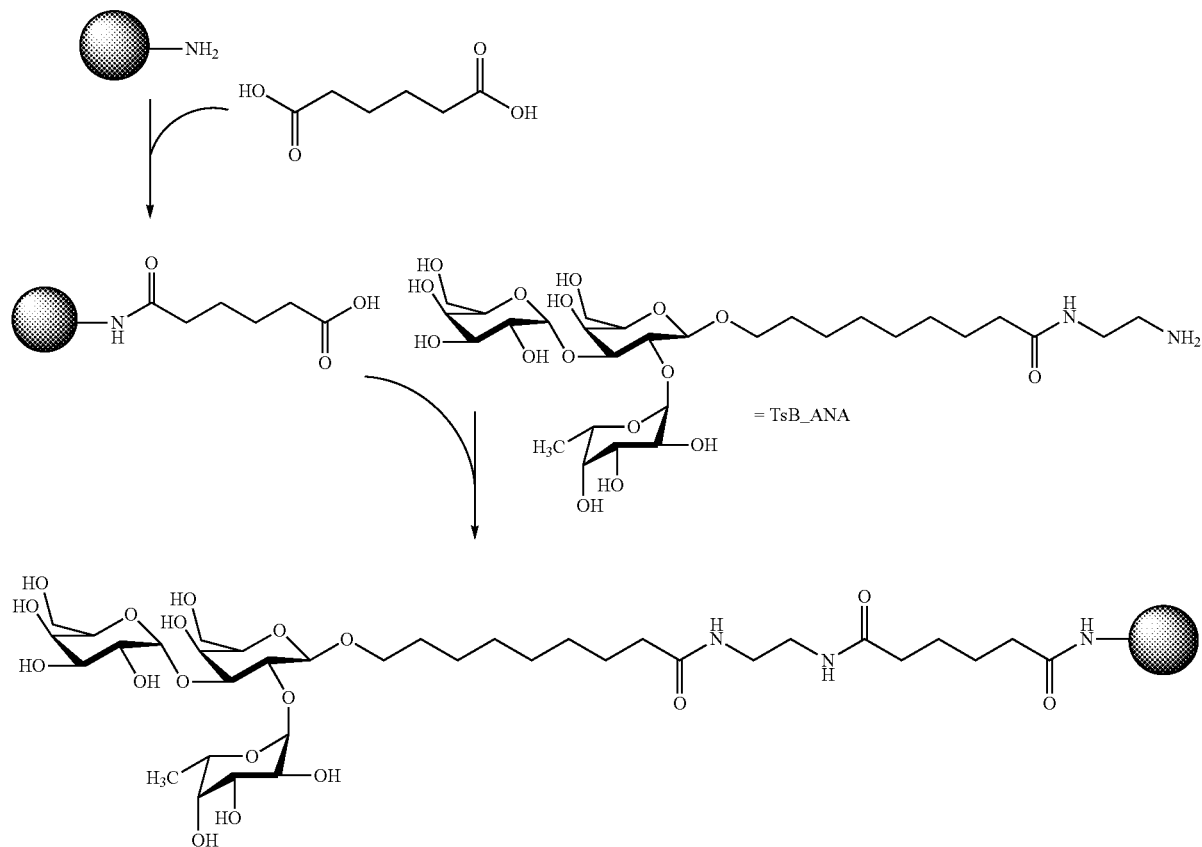

Example 3

Reaction of an Epoxy-Functionalized Matrix with Aminoheaxanoic Acid and Coupling of a Blood Group B Trisaccharide The separating material of the present invention is produced by using beads having epoxy functions (Tosoh Toyopearls AF-Epoxy 650-M, ChiralVision IB-350 or Mitsubishi ReliZyme™ EXE 135). Hence, a compound of formula (III) having an amino function can directly react with the epoxy function of the matrix. Here, the compound of formula (III) is aminohexanoic acid. The amino function leads to an epoxy opening, while at the same time a carbon-nitrogen bond is formed. In the second step the remaining free carboxy function of the aminohexanoic acid can be coupled to a saccharide of formula (V) having a free amino function, ("TsB_ANA", see Example 2).

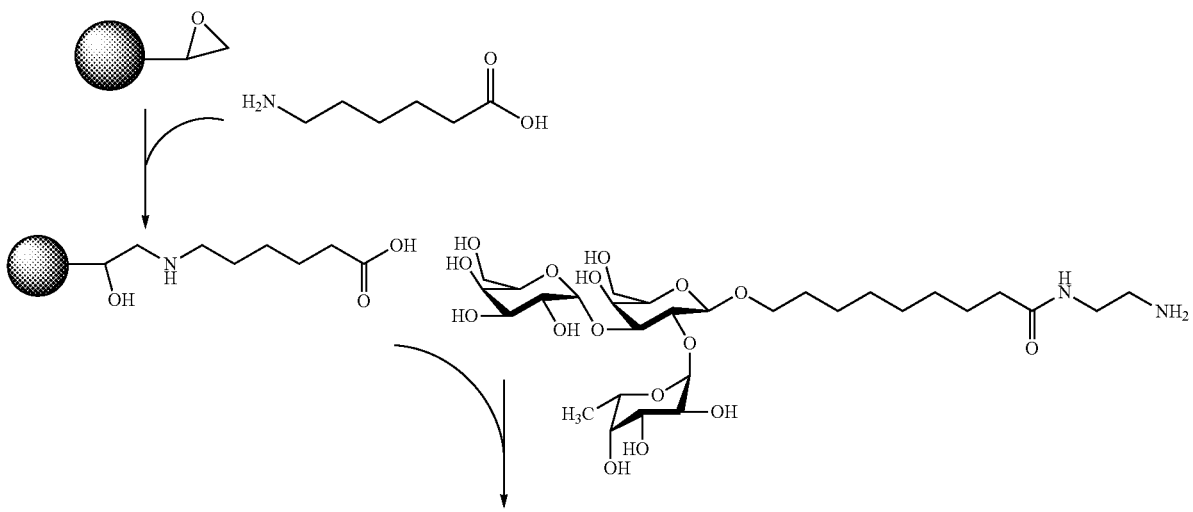

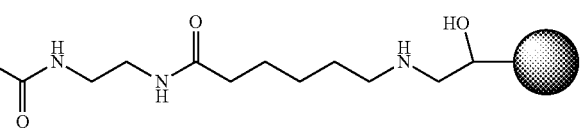
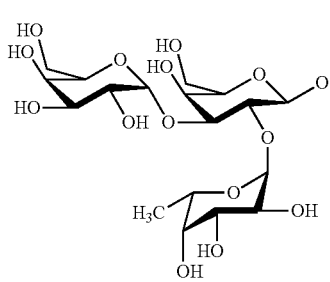

Example 4

Reaction of an Amino-Functionalized Matrix a Blood Group B Trisaccharide

The separating material of the present invention is produced by using beads having amino functions (e.g. Tosoh Toyopearls® AF-Amino 650-M). Here, the carboxy function of a saccharide of formula (V) is directly coupled to the amino function of the matrix (IV).

Example 6

Polyelectrolyte Titration

The analysis of the coupling reactions between the compound of formula (III) and the matrix of formula (IV) is carried out by quantifying the charges present due to the coupling of a compound of formula (III). The polyelectrolyte used is cationic polydiallyldimethylammonium chloride (poly-DADMAC) and anionic sodium polyethylensulfonate.

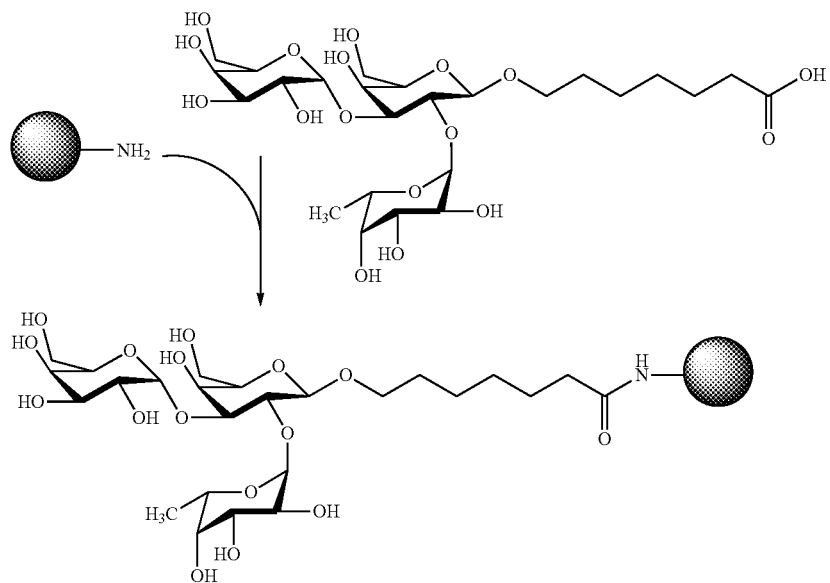

Example 5

Resorcinol Test

The quantitative analysis of the amount of saccharide, such as the trisaccharide in Examples 1 to 4, which has been bound to a matrix is carried out by the resorcinol test according to Monsigny et al. (*Analytical Biochemistry* 175, 1988, 525-530). 3 mg dry TsB-beads are given into a glass tube together with 200 µL distilled water, 200 µL of an aqueous resorcinol solution (60 mg resorcinol in 10 mL water) and 1 mL of sulphuric acid 75%. The mixture is stirred and heated at 90° C. for 30 min, followed by cooling in a water bath for 30 min in the absence of light, followed by centrifugation. The saccharide content is calculated by measuring the absorption of the solution at 503 nm in a UV/VIS-spectrometer, subtraction of the blank and evaluating the result on a previously created calibration curve.

The polyelectrolyte titration is carried out with a BTG Mütek PCD-03 Particle Charge Detector.

In case of anionic functional groups on the matrix, 100 mg are stirred overnight with 60 mL 0.001M poly-DADMAC solution at pH 12. 1 mL of the reaction solution is then titrated in the PCD-03 with 0.001 N sodium polyethylenesulfonate.

Example 7

Transformation of Epoxy Functions on Epoxy-Beads into β-amino Alcohols

Epoxy beads (Toyopearl AF Epoxy 650M, Chiralvision Immobeads T2-150, and ReliZyme™ EXE 135, respectively) were incubated overnight at room temperature with a 32.0 wt-% ammonia solution in water, in order to transform the epoxy functions into β-amino alcohols. Per gram of beads, 8 mL ammonia solution were applied. In the next step, the beads were rinsed over a glass filter with reverse osmosis water to a neutral pH.

Example 8

Coupling Procedure for Amino-Functionalized Beads with Dicarboxylic Acids

For coupling the dicarboxylic compound of formula (III) to amino functionalized beads, a triple excess of the dicarboxylic acid, for instance, glutaric, adipic acid or glutathione, with respect to the initial functionalization of the beads was solved in a 0.5 M phosphate buffer at pH 5.4, followed by addition of a six fold excess of a coupling reagent, e.g. EDC or DIC in combination with NHS. The beads were incubated overnight at room temperature with this coupling solution and finally rinsed with reverse osmosis water over a glass filter. The concentration of carboxylic acid groups on the beads was determined by polyelectrolyte titration. The results of Examples 8 and 9 are summarized in table III below.

TABLE III

Coupling efficiency of glutaric acid and glutathione to functionalized beads.

| Matrix | Compound of Formula (III) | μmol/g (uncoupled) | μmol/g (coupled) |
|---|---|---|---|
| Toyopearl ® AF Epoxy 650M (amino-functionalized) | glutaric acid | 800 | 382 |
| Toyopearl ® AF Epoxy 650M (amino-functionalized) | glutathione | 800 | 348 |
| ReliZyme ™ EXE 135 (amino-functionalized) | glutaric acid | 166 | 119 |
| Immobead ™ IB-350 (amino-functionalized) | glutaric acid | 100 | 53 |
| Immobead ™ T2-150 (amino-functionalized) | glutaric acid | 100 | 109 |

Example 9

Coupling of Glutaric Acid to Aminated ReliZyme™ EXE 135

1 g beads (ReliZyme™ EXE 135, 1 eq., 166 μmol/g) of Example 7 were given to a solution of 66.2 mg glutaric acid (3 eq.) and 192 mg EDC (6 eq.) in 5 mL 0.1 M MES buffer at pH 5.4. The beads were stirred over a rotating platform for 24 h at room temperature, followed by rinsing of the beads with reverse osmosis water. The functionalization of the beads with carboxy functions was determined by polyelectrolyte titration to 119 μmol/g beads.

Example 10

Coupling of 6-aminohexanoic acid to ReliZyme™ EXE 135

1 g beads ReliZyme™ EXE 135 (1 eq., 166 μmol/g), bearing epoxy functions, in 5 mL 0.1 M borate-KCl buffer (pH 13), was reacted with 65.7 mg 6-aminohexanoic acid (3 eq.) for 24 h at 40° C., followed by a rinsing step. The functionalization of the beads with carboxy functions was determined by polyelectrolyte titration to 154 μmol/g beads.

Example 11

Coupling of Blood Group Determinant B Trisaccharides to the Coupling Products of Matrix (IV) and Compounds of Formula (III)

An equimolar amount of blood group determinant B trisaccharide with respect to the initial functionalization of the beads was solved in 0.1 M MES-buffer, pH 5.4. To this solution, 2 equivalents of coupling agent EDC were added, followed by the addition of the beads of Example 8, incubation overnight at room temperature and a final rinsing step with reverse osmosis water, obtaining beads functionalized with blood group B trisaccharides (TsB-beads). The functionalization of the beads with TsB in terms of μmol of the saccharide per g of bead was analysed by the resorcinol test (Table IV).

TABLE IV

Coupling of blood group determinant B trisaccharides to functionalized matrices

| Beads | linker | TsB_AP | TsB_ANA | μmol TsB/g beads |
|---|---|---|---|---|
| Toyopearl ® AF-Carboxy 650M | — | | x | 38.9-40.2 |
| Toyopearl ® AF Epoxy 650M | glutaric acid | x | | 8.9-9.2 |
| Toyopearl ® AF Epoxy 650M | glutaric acid | | x | 26.1-48.3 |
| Toyopearl ® AF Epoxy 650M | glutathione | x | | 4.9 |
| Toyopearl ® AF Epoxy 650M | — | | x | 5.6-10.9 |
| ReliZyme ™ EXE 135 | glutaric acid | | x | 8.5 |
| Immobeads ™ IB-350 | glutaric acid | | x | 1.6-2.7 |
| Immobeads ™ T2-150 | glutaric acid | | x | 7-7.3 |

Example 12

Coupling of TsB_ANA to Glutaric Acid Functionalized ReliZyme™ EXE 135 Beads 6.1 μmol TsB_ANA were solved in 0.5 mL 0.1 M MES buffer pH 5.4. To this solution, 96 mg EDC (3 eq. with respect to the initial functionalization of the beads) were added, followed by the addition of 40 mg functionlaized ReliZyme™ EXE 135 beads of Example 9, stirring over a rotating platform for 24 h at room temperature and final rinsing step with reverse osmosis water, obtaining TsB-functionalized beads. The functionalization of the beads with saccharide was determined by a resorcinol test to be 8.5 μmol TsB_ANA/g beads.

Example 13

Coupling of TsB_ANA to 6-aminohexanoic acid bound to ReliZyme™ EXE 135 beads 6.1 μmol TsB_ANA were solved in 0.5 mL 0.1 M MES buffer pH 5.4. To this solution, 96 mg EDC (3 eq. with respect to the start functionalization of the beads) were added, followed by the addition of 40 mg functionalized ReliZyme™ EXE 135 beads of Example 10, stirring over a rotating platform for 24 h at room temperature and a final rinsing step with reverse osmosis water, obtaining TsB-functionalized beads. The functionalization of the beads with saccharide was determined by a resorcinol test to be 25.9 μmol TsB_ANA/g beads.

Example 14

Coupling of TsB_AP to Glutaric Acid Bound to Toyopearl AF Epoxy 650M Beads 131.3 mg TsB_AP (1 eq) were solved in 7 mL phosphate buffer, pH 5.4. To this solution, 70.4 mg DIC (3 eq.) were added, followed by the addition of 161.7 mg functionalized Toyopear® AF Epoxy 650M beads of Example 8, stirring over a rotating platform for 24 h at room temperature and a final rinsing step with reverse osmosis water, obtaining TsB-beads.

Example 15

Coupling of TsB_ANA to Glutaric Acid Bound to Toyopearl AF Epoxy 650M Beads 725 mg NHS, 0.981 mL DIC and 0.893 mL diisopropylethylamine were solved in 25 mL 1,4-dioxane. 0.5 g functionalized Toyopear® AF Epoxy 650M beads of Example 8 were added to 2.5 mL of the activating solution and stirred over a rotating platform for 3 h at room temperature. The beads were then washed with 5 mL 1,4-dioxane and 15 mL DMSO. 14.4 mg TsB_ANA in 2 mL DMSO were added to the beads, followed by stirring the suspension over a rotating platform for 3 h at room temperature and rinsing the beads with reverse osmosis water. The functionalization of the beads with saccharide was determined by a resorcinol test to be 43.4 μmol TsB_ANA/g beads.

Example 16

Coupling of TsB_ANA to Glutaric Acid Functionalized Chiralvision Immobead™ T2-150 Beads 4.3 mg TsB_ANA (0.1 eq) were solved in 2 mL phosphate buffer pH 5.4. To this solution, 18.9 mg DIC (3 eq.) were added, followed by the addition of 0.5 g functionalized Immobead™ T2-150 beads (1 eq) of Example 8, stirring over a rotating platform for 24 h at room temperature and a final rinsing step with reverse osmosis water, obtaining TsB-beads. The functionalization of the beads with saccharide was determined by a resorcinol test to be 7.1 μmol TsB_ANA/g beads.

Example 17

Antibody Titer Reduction with TsB-Beads 0.5 mL blood group A plasma was added to 20 mg wet TsB-beads of Examples 11-15, which roughly corresponds to 5 mg dry beads, and was incubated at 37° C. for 120 min over a rotating platform. The probe was then centrifuged (10 min at 1000 g) and the supernatant was used for the determination of IgM antibody titer with a gel test assay which is commercially available from Bio-Rad Laboratories (NaCl, Enzyme Test and Cold Agglutinins ("NaCl cards"); Coombs Anti-IgG ("Coombs cards")). Therefore, serial dilutions of the probe were prepared. 50 μL of plasma or plasma dilution, respectively, were mixed with 50 μL erythrocytes B in NaCl cards and were incubated 15 min at room temperature. In the next step, the probes were centrifuged in an ID-centrifuge (DiaMed AG) and the gel cards were evaluated with regard to agglutination.

Similarly, the IgG antibody titer was determined. First, serial dilutions of the probes were prepared. Then, 50 μL of plasma or plasma dilution, respectively, were mixed with 50 μL erythrocytes B in Coombs cards and were incubated 15 min at room temperature. In the next step, the probes were centrifuged in an ID-centrifuge (DiaMed AG) and the gel cards were evaluated with regard to agglutination.

Tables V to XIV summarize the results with beads.

IgM

TABLE V

Tosoh Toyopearl ® AF-Epoxy 650-M + ammonia

|  | Start titer | End titer |
| --- | --- | --- |
| Glutaric acid + TsB_ANA | 1:512 | 1:2 |
| Glutaric acid + TsB_AP | 1:512 | 1:4 |
| Adipic acid + TsB_AP | 1:64 | 1:4 |
| DC-PEG + TsB_AP | 1:512 | 1:2 |

IgG

TABLE VI

Tosoh Toyopearl ® AF-Epoxy 650-M + ammonia

|  | Start titer | End titer |
| --- | --- | --- |
| Glutaric acid + TsB_Ana | 1:256 | 1:2 |
| Glutaric acid + TsB_AP | 1:1024 | 1:4 |
| Adipic acid + TsB_AP | 1:64 | 1:4 |
| DC-PEG + TsB_AP | 1:256 | 1:2 |

IgM

TABLE VII

Tosoh Toyopearl ® AF-Amino 650-M

|  | Start titer | End titer |
| --- | --- | --- |
| Glutaric acid + TsB_AP | 1:1024 | 1:8 |

IgG

TABLE VIII

Tosoh Toyopearl ® AF-Amino 650-M

|  | Start titer | End titer |
| --- | --- | --- |
| Glutaric acid + TsB_AP | 1:512 | 1:8 |

IgM

TABLE IX

ChiralVision IB ™-350 + ammonia[a]

|  | Start titer | End titer |
| --- | --- | --- |
| Glutaric acid + TsB_AP | 1:64 | 1:16 |
| Glutaric acid + TsB_ANA | 1:64 | 1:8 |

[a]100 mg beads/0.5 mL plasma were used

IgG

TABLE X

| ChiralVision IB ™-350 + ammonia[a] | | |
|---|---|---|
| | Start titer | End titer |
| Glutaric acid + TsB_AP | 1:64 | 1:16 |
| Glutaric acid + TsB_ANA | 1:64 | 1:4 |

[a] 100 mg beads/0.5 mL plasma were used

IgM

TABLE XI

| ReliZyme ™ EXE 135 + ammonia | | |
|---|---|---|
| | Start titer | End titer |
| Glutaric acid + TsB_ANA | 1:64 | 1:4 |

IgG

TABLE XII

| ReliZyme ™ EXE 135 + ammonia | | |
|---|---|---|
| | Start titer | End titer |
| Glutaric acid + TsB_ANA | 1:64 | 1:2 |

IgM

TABLE XIII

| ReliZyme ™ EXE 135 | | |
|---|---|---|
| | Start titer | End titer |
| 6-aminohexanoic acid + TsB_ANA | 1:64 | 1:1 |

IgG

TABLE XIV

| ReliZyme ™ EXE 135 | | |
|---|---|---|
| | Start titer | End titer |
| 6-aminohexanoic acid + TsB_ANA | 1:64 | 1:1 |

Example 18

Antibody Titer Reduction Test with a Dilution Series of TsB_ANA 65.7 mg 6-aminohexanoic acid (3 eq.) were added to a suspension of 1 g (0.167 mmol, 1 eq.) epoxide beads (ReliZyme™ EXE 135) in 5 mL 0.1 M borate-KCl buffer, pH 10. After adjusting the pH at 13, the mixture was stirred at 40° C. for 24 h, followed by filtration and rinsing with distilled water. The concentration of carboxylic functions on the beads was determined, by polyelectrolyte titration, to be 0.167 mmol/g which corresponds to a complete conversion of the epoxide functions.

240 mg (2.09 mmol) NHS and 325 μL (2.09 mmol) DIC were solved in 10 mL 1,4-dioxane. 0.25 g beads (42 μmol, 1 eq.) were added to 1 mL of the activating solution containing 5 eq. of NHS and DIC. The mixture stirred over a rotating platform for 3 h at room temperature, followed by rinsing the beads with 5 mL 1,4-dioxane and 15 mL DMSO.

For the coupling of the activated beads with a trisaccharide, a stock solution of TsB_ANA in DMSO was prepared. Therefore, 8.72 μmol, 6.0 mg TsB_ANA were dissolved in 1 ml DMSO. Starting from this stock solution, 4 different coupling reactions with 4 different amounts of TsB_ANA were carried out. The reaction conditions are summarized in table XV.

TABLE XV

| Exp | Beads [g] | Stock solution [μL] | DMSO [μL] | μmol TsB/ g beads |
|---|---|---|---|---|
| 8_0 | 0.25 | 500 | 0 | 17.5 |
| 8_1 | 0.25 | 286 | 214 | 10 |
| 8_2 | 0.25 | 143 | 357 | 5 |
| 8_3 | 0.25 | 28.6 | 471.4 | 1 |

Therefore, the beads were added to a mixture of TsB stock solution and a corresponding volume of DMSO, followed by stirring on a rotating platform for 24 h at room temperature and rinsing with reverse osmosis water. The Resorcinol test showed 100% coupling of the trisaccharide to the beads.

With theses four saccharide-functionalized beads, IgM and IgG titer reduction tests were carried out as described in Example 17. The results are summarized in table XVI.

TABLE XVI

| Exp. | IgM | IgG |
|---|---|---|
| Start titer | 1:64 | 1:64 |
| 8_0 | 1:4 | 1:2 |
| 8_1 | 1:8 | 1:4 |
| 8_2 | 1:16 | 1:32 |
| 8_3 | 1:64 | 1:64 |

Example 19

Plasma Functionalization of a Hollow Fiber Membrane 1000 m of a porous polyaryethersulfone-polyvinylpyrrolidone hollow fiber membrane with an outer shell diameter of 320 μm and a wall thickness of 50 μm were fed through the vacuum sealed plasma ignition chamber with a velocity of 5-20 m/min. Into said ignition chamber a precursor gas consisting of ammonia with a pressure of 0.25 mbar was introduced with a view to depositing an amine containing carbohydrate thin film on the porous surface of the membrane. The plasma was excited with a 13.56 MHz pulsed RF power of 100 W. After this plasma treatment the density of amino groups was measured by polyelectrolyte titration, wherein a value of 20 μmol/g was found.

FIG. 1 shows the result of a two photon excitation microscopy experiment on a hollow fiber membrane having a wall thickness of 50 μm. The amino functions on the membrane formed by plasma functionalization were first reacted with a fluorophore, here 4-fluoro-7-nitrobenzo-2-oxa-1,3-diazole (NBD-F). The excitation occurred by two photons of comparably lower energy than needed for one photon excitation. Each photon carries approximately half the energy necessary to excite the molecule. An excitation results in the subsequent emission of a fluorescence photon, typically at a higher energy than either of the two excitatory photons. The image shows that amino functions are present on the outer surface and within the adjacent 20 μm of the wall. Hence, 40% of the wall is functionalized with amino functions.

Example 20

Preparation of Mini Modules

The preparation of membrane bundles after the spinning process is necessary to prepare the fiber bundle in an adequate way for the experiments. The first process step is to fix 150 fibers near their ends by a filament. The fiber bundle is transferred into a housing. Then, the fiber bundle is cut to a defined length of 20 cm. The next process step consists of transferring the fibers into a potting cap. The potting cap is fixed mechanically, and a potting tube is put over the potting caps. Then, the ends of the fibers are closed. An optical control ensures that all fibers are well closed. Afterwards, the mini module is put into a vacuum drying oven over night before. Then, the potting is done with polyurethane. After the potting, it has to be ensured that the polyurethane can harden for at least one day. In the next process step, the potted membrane bundle is cut to a defined length. The last process step consists of an optic control of the fiber bundle. During this process step, the quality of the cut (is the cut smooth or are there any damages of the knife) and the quality of the potting (is the number of open fibers of the spinning process reduced by fibers that are potted or are there any visible voids where there is no polyurethane) are controlled. After the optical control, the membrane bundles are stored dry before they are used for the different experiments.

Example 21

Preparation of Filters

The filter (=dialyzer) comprises about 8,000 to 10,000 fibers with an effective surface area of 1.4 m². A filter is characterized by a cylindrical housing with two connectors for the dialyzing fluid and caps applied on both ends, each with one centered blood connector. The manufacturing process (after winding) can be divided into the following main steps:
(A) the cut bundles (length approx. 30 cm) are transferred into the housing with a special bundle claw;
(B) both ends of the bundles are closed by a closing process
(C) the fibers are potted into the housing with polyurethane (PUR);
(D) the ends are cut to open the fibers;
(E) the caps are welded to the blood connectors using ultrasonic welding;
(F) final treatment comprises: rinsing, integrity testing, final drying
(G) the filters are packed in sterile bags and steam sterilized.

Example 22

Coupling of Glutaric Acid to Amino-Functionalized Hollow Fiber Membranes

For coupling the hollow fibers of Example 19 to a compound of formula (III), 30 g glutaric acid and 30 g EDC were dissolved in 1500 mL 0.25 M phosphate buffer, pH 5.4. This solution was used to functionalize four mini modules with 150 fibers each. The coupling was carried out by circulating the solution through the 4 mini modules at a flow rate of 85 mL/min at room temperature for 16 h. Then, the modules were rinsed with 40 L reverse osmosis water and were finally dried. The functionalization was measured by polyelectrolyte titration to be 9.4 μmol/g.

Example 23

Coupling of TsB to Glutaric Acid Attached to Hollow Fiber Membranes

For coupling blood group B trisaccharide (TsB) to the hollow fibers (200 mg) of Example 22, 10 μmol (2.5 eq.) TsB_AP and TsB_ANA, respectively, and 25 μmol coupling agent EDC were dissolved in 17 mL 0.1 M MES buffer, pH 5.4 for every mini module. The coupling was carried out at continuous flow conditions at a flow rate of 6 mL/min at room temperature for 24 h. Then, the modules were rinsed with 1.5 L reverse osmosis water and were finally dried.

Example 24

Antibody Titer Reduction Test with TsB-Hollow Fibers

A mini module comprising 150 hollow fibers of Example 23 was perfused with a mixture of 10 mL human plasma of blood group A and 10 mL NaCl-solution in a tempered hood at 37° C. for 2 h at a flow rate of 2.5 mL/h and a 40% filtration. Probes were taken from the resulting pool with which the determination of IgM antibody titer with a gel test assay from Bio-Rad Laboratories, see above, was carried out. Therefore, serial dilutions of the probes were prepared. 50 μL of plasma or plasma dilution, respectively, were mixed with 50 μL erythrocytes B in NaCl cards and were incubated 15 min at room temperature. In the next step, the probes were centrifuged in an ID-centrifuge (DiaMed AG) and the gel cards were evaluated with regard to agglutination.

Similarly, the IgG antibody titer was determined. First, serial dilutions of the probes were prepared. Then, 50 μL of plasma or plasma dilution, respectively, were mixed with 50 μL erythrocytes B in Coombs cards and were incubated 15 min at room temperature. In the next step, the probes were centrifuged in an ID-centrifuge (DiaMed AG) and the gel cards were evaluated with regard to agglutination.

The results are summarized in the following tables XVII and XVIII. They show that a longer linker leads to a more effective titer reduction.

IgM

TABLE XVII

| Hollow fibers + ammonia plasma | | |
|---|---|---|
|  | Start titer | End titer |
| Glutaric acid + TsB_AP | 1:32 | 1:32 |
| Glutaric acid + TsB_ANA | 1:32 | 1:16 |

IgG

TABLE XVIII

| Hollow fibers + ammonia plasma | | |
|---|---|---|
|  | Start titer | End titer |
| Glutaric acid + TsB_AP | 1:32 | 1:32 |
| Glutaric acid + TsB_ANA | 1:32 | 1:8 |

Example 25

Comparison of Antibody Titer Reduction with Separation Material Comprising TsB, Based on Different Matrices, Linker Concentrations and Reaction Conditions

Example 25A

ReliZyme™ EXE 135 with Varying Amounts of Saccharide (A) Coupling of the Linker 65.7 mg 6-aminohexanoic acid (3 equivalent) were added to a suspension of 1 g (0.167 mmol, 1 equivalents) epoxide beads (ReliZyme™ EXE 135) in 5 mL 0.1 M borate-KCl buffer, pH 10. After adjusting the pH at 13 with 0.1 M NaOH, the mixture was stirred at 40° C. for 24 h, followed by filtration and rinsing with distilled water. The concentration of carboxylic functions on the beads was determined, by polyelectrolyte titration, to be 165 μmol/g of the beads.

(B) Activation Step 14.4 mg N-hydroxysuccinimide (NHS) and 24.0 mg 1-ethyl-3-(3'-dimethylaminopropyl)carbodiimide*HCl (EDC, 3 ep.) were solved in 1 mL polyethyleneglycol 200 (PEG-200) together with 0.25 g beads (0.167 mmol, 1 eq.) of step (A). The mixture was stirred over a rotating platform for 3 h at room temperature, followed by filtration and rinsing with 20 ml PEG-200.

(C) Coupling of the Saccharide

For the coupling of the activated beads of step (B) with a trisaccharide, various amounts of TsB_ANA were prepared (3.3 mg, 2.3 mg, 1.7 mg, 1.4 mg) as shown in Table XIX below and dissolved in 0.5 ml PEG-200. 4 different coupling reactions with 4 different amounts of TsB_ANA were carried out. The mixtures were stirred over a rotating platform for 24 h at room temperature, respectively, followed by filtration and rinsing with distilled water. The reaction conditions are otherwise summarized in table XIX, including the degree of conversion, i.e. coupling rate of the saccharide. The titer reduction was done as described above, with 20 mg of wet TsB-beads (corresponding to 5 mg of the dry material) and 1.5 mL human plasma.

TABLE XIX

| Exp. | TsB_ANA (initial con.) [μmol/g beads] | Concentration of 6-AHS on the beads [μmol/g beads] | Concentration of TsB on the beads [μmol/g beads] | Degree of Conversion [%] | Titer Reduction in steps |
|---|---|---|---|---|---|
| 183 | 19.2 | 165 | 12.5 | 65 | 6-4 |
| 184 | 13.4 | 165 | 9.6 | 72 | 5-4 |
| 185 | 9.9 | 165 | 7.1 | 72 | 5-4 |
| 186 | 8.2 | 165 | 6.4 | 78 | 4-3 |

Example 25B

ReliZyme™ EXE 135 with Constant Amounts of Saccharide and Varying Reaction Parameters (A) Coupling of the Linker 65.7 mg 6-aminohexanoic acid (3 equivalent) were added to a suspension of 1 g (0.167 mmol, 1 equivalents) epoxide beads (ReliZyme™ EXE 135) in 5 mL 0.1 M borate-KCl buffer, pH 10. After adjusting the pH at 10 or 13 with 0.1 M NaOH, the mixture was stirred at 40° C. or 55° C. for 6 h or 24 h, respectively, followed by filtration and rinsing with distilled water until the pH was neutral. The concentration of carboxylic functions on the beads was determined, by polyelectrolyte titration. Results are shown in Table XX.

(B) Activation Step 14.4 mg N-hydroxysuccinimide (NHS) and 24.0 mg 1-ethyl-3-(3'-dimethylaminopropyl)carbodiimide*HCl (EDC, 3 ep.) were solved in 1 mL polyethyleneglycol 200 (PEG-200) together with 0.25 g beads (0.167 mmol, 1 eq.) of step (A). The mixture was stirred over a rotating platform for 3 h at room temperature, followed by filtration and rinsing with 20 ml PEG-200.

(C) Coupling of the Saccharide

For the coupling of the activated beads of step (B) with a trisaccharide, 3 mg (±0.1) of TsB_ANA were prepared and dissolved in 0.5 ml PEG-200, respectively. 6 different coupling reactions with essentially the same amounts of TsB_ANA were carried out as ser forth in Table XX. The mixtures were stirred over a rotating platform for 24 h at room temperature, respectively, followed by filtration and rinsing with distilled water. The reaction conditions are otherwise summarized in table XIX, including the degree of conversion, i.e. coupling rate of the saccharide. The titer reduction was done as described above, with 20 mg of wet TsB-beads (corresponding to 5 mg of the dry material) and 1.5 mL human plasma.

TABLE XX

| Exp. | Reaction parameters (Step A) | TsB_ANA (initial con.) [μmol/g beads] | Conc. of 6-AHS on the beads [μmol/g beads] | Conc. of TsB on the beads [μmol/g beads] | Degree of Conversion [%] | Titer Reduction in steps |
|---|---|---|---|---|---|---|
| 188 | 55° C., 24 h, pH 13 | 18.0 | 190 | 14.0 | 78 | 5-3 |
| 190 | 40° C., 24 h, pH 13 | 18.0 | 171 | 14.0 | 78 | 6-3 |
| 191 | 55° C., 6 h, pH 13 | 18.0 | 141 | 12.2 | 68 | 5-4 |
| 189 | 40° C., 6 h, pH 13 | 17.5 | 107 | 14.1 | 80 | 5-4 |
| 199 | 40° C., 24 h, pH 10 | 17.5 | 60 | 9.7 | 55 | 1-2 |
| 198 | 40° C., 6 h, pH 10 | 16.7 | 30 | 7.2 | 43 | 1-2 |

Example 25C

ReliZyme™ EXE 148 with Varying Amounts of Saccharide (A) Coupling of the Linker 85.8 mg 6-aminohexanoic acid (3 equivalent) were added to a suspension of 1 g (0.218 mmol, 1 equivalents) epoxide beads (ReliZyme™ EXE 148) in 5 mL 0.1 M borate-KCl buffer, pH 10. After adjusting the pH at 13 with 4 mL 0.1 M NaOH, the mixture was stirred at 40° C. for 24 h, followed by filtration and rinsing with distilled water until the pH reached neutral value. The concentration of carboxylic functions on the beads was determined, by polyelectrolyte titration, to be 285 μmol/g of the beads.

(B) Activation Step 14.4 mg N-hydroxysuccinimide (NHS) and 24.0 mg 1-ethyl-3-(3'-dimethylaminopropyl)carbodiimide*HCl (EDC, 3 eq.) were solved in 1 mL polyethyleneglycol 200 (PEG-200) together with 0.25 g beads (0.285 mmol, 1 eq.) of step (A). The mixture was stirred over a rotating platform for 3 h at room temperature, followed by filtration and rinsing with 20 ml PEG-200.

(C) Coupling of the Saccharide

For the coupling of the activated beads of step (B) with a trisaccharide, various amounts of TsB_ANA were prepared (3.0 mg, 2.2 mg, 1.9 mg, 1.6 mg) as shown in Table XIX below and dissolved in 0.5 ml PEG-200. 4 different coupling reactions with 4 different amounts of TsB_ANA were carried out. The mixtures were stirred over a rotating platform for 24 h at room temperature, respectively, followed by filtration and rinsing with distilled water. The reaction conditions are otherwise summarized in table XXI, including the degree of conversion, i.e. coupling rate of the saccharide. The titer reduction was done as described above, with 20 mg of wet TsB-beads (corresponding to 5 mg of the dry material) and 1.5 mL human plasma.

TABLE XXI

| Exp. | TsB_ANA (initial conc.) [μmol/g beads] | Concentration of 6-AHS on the beads [μmol/g beads] | Concentration of TsB on the beads [μmol/g beads] | Degree of Conversion [%] | Titer Reduction in steps |
|---|---|---|---|---|---|
| 179 | 17.5 | 285 | 13.2 | 76 | 7-6 |
| 180 | 12.8 | 285 | 10.8 | 84 | 6-5 |
| 181 | 11.1 | 285 | 9.2 | 83 | 6-5 |
| 182 | 9.3 | 285 | 6.9 | 74 | 5-4 |

Example 25D

ReliZyme™ EXE 148 with Constant Amounts of Saccharide and Varying Reaction Parameters (A) Coupling of the Linker 85.8 mg 6-aminohexanoic acid (3 equivalent) were added to a suspension of 1 g (0.167 mmol, 1 equivalents) epoxide beads (ReliZyme™ EXE 148) in 5 mL 0.1 M borate-KCl buffer, pH 10. After adjusting the pH at 10 or 13 with 4 mL NaOH, the mixture was stirred at 40° C. or 55° C. for 6 h or 24 h, respectively, followed by filtration and rinsing with distilled water until the pH was neutral. The concentration of carboxylic functions on the beads was determined, by polyelectrolyte titration. Results are shown in Table XXII.

(B) Activation Step 14.4 mg N-hydroxysuccinimide (NHS) and 24.0 mg 1-ethyl-3-(3'-dimethylaminopropyl)carbodiimide*HCl (EDC, 3 eq.) were solved in 1 mL polyethyleneglycol 200 (PEG-200) together with 0.25 g beads (0.285 mmol, 1 eq.) of step (A). The mixture was stirred over a rotating platform for 3 h at room temperature, followed by filtration and rinsing with 20 ml PEG-200.

(C) Coupling of the Saccharide

For the coupling of the activated beads of step (B) with a trisaccharide, 3 mg (±0.1) of TsB_ANA were prepared and dissolved in 0.5 ml PEG-200, respectively. 6 different coupling reactions with essentially the same amounts of TsB_ANA were carried out as ser forth in Table XX. The mixtures were stirred over a rotating platform for 24 h at room temperature, respectively, followed by filtration and rinsing with distilled water. The reaction conditions are otherwise summarized in table XIX, including the degree of conversion, i.e. coupling rate of the saccharide. The titer reduction was done as described above, with 20 mg of wet TsB-beads (corresponding to 5 mg of the dry material) and 1.5 mL human plasma.

TABLE XXII

| Exp. | Reaction parameters (Step A) | TsB_ANA (initial quantity) [μmol/g beads] | Conc. of 6-AHS on the beads [μmol/g beads] | Conc. of TsB on the beads [μmol/g beads] | Degree of Conversion [%] | Titer Reduction in steps |
|---|---|---|---|---|---|---|
| 195 | 55° C., 24 h, pH 13 | 17.5 | 263 | 13.8 | 79 | 8-7 |
| 194 | 55° C., 6 h, pH 13 | 18.0 | 229 | 12.3 | 68 | 7-6 |
| 193 | 40° C., 6 h, pH 13 | 18.0 | 176 | 14.0 | 78 | 6-5 |
| 192 | 40° C., 24 h, pH 10 | 18.0 | 148 | 12.3 | 68 | 5-4 |
| 197 | 55° C., 6 h, pH 10 | 17.5 | 108 | 10.2 | 58 | 5-3 |
| 196 | 40° C., 6 h, pH 10 | 17.5 | 78 | 6.9 | 39 | 3-2 |

The invention claimed is:

1. A separation material comprising a saccharide-linker-matrix represented by a general formula of
saccharide-linker-matrix, wherein the linker is chosen from the group of linkers consisting of
—X(CH$_2$)$_s$—NH—CO—(CH$_2$)$_s$—CONH—,
—X(CH$_2$)$_s$—CO—NH—(CH$_2$)$_s$—NH—CO—(CH$_2$)$_s$—CONH—,
—X(CH$_2$)$_s$—NH—CO—CH$_2$—(O—C$_2$H$_4$)$_l$—O—CH$_2$—CONH—,
—X(CH$_2$)$_s$—CO—NH—(CH$_2$)$_s$—NH—CO—CH$_2$—(O—C$_2$H$_4$)$_l$—O—CH$_2$—CONH—,
—X(CH$_2$)$_s$—CONH—,
—X(CH$_2$)$_s$—NH—CO—(CH$_2$)$_s$—CO—NH—(CH$_2$)$_s$—NH—CO—(CH$_2$)$_s$—CONH—,
—X(CH$_2$)$_s$—CO—NH—(CH$_2$)$_s$—NH—CO—(CH$_2$)$_s$—CO—NH—(CH$_2$)$_s$—NH—CO—(CH$_2$)$_s$—CONH—,
—X(CH$_2$)$_s$—CO—NH—(CH$_2$)$_s$—NH—CO—(CH$_2$)$_s$—NH—CH$_2$—CH(OH)—,
—X(CH$_2$)$_s$—NH—CO—(CH$_2$)$_s$—NH—CH$_2$—CH(OH)—,
—X(CH$_2$)$_s$—CO—NH—(CH$_2$)$_s$—NH—CO—CH(NH$_2$)—(CH$_2$)$_2$—CO—NH—CH(SH)—CO—NH—CH$_2$—CO—NH—CH$_2$—CH(OH)—,
wherein
X represents O, N, S or CH$_2$; and
s represents, independently of one another, an integer from 1-10, and
l represents an integer from 1-600.

2. The separation material according to claim 1 wherein the matrix is a synthetic polymer, a peptide or a polysaccharide.

3. The separation material according to claim 1, wherein the matrix is prepared from hydrophilic and/or hydrophobic synthetic polymers selected from the group consisting of polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), poly-acrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PAES), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine and copolymers thereof.

4. The separation material according to claim 2 wherein the matrix is prepared from hydrophilic and/or hydrophobic synthetic polymers selected from the group consisting of polyacrylates (PA), poly(methyl methacrylate) (PMMA) or polyglycidyl methacrylate (PGMA), polyvinylpyrrolidone (PVP), polysulfone (PS), polyethersulfone (PES), polyarylethersulfone (PAES) and combinations thereof.

5. The separation material according to claim 2 wherein the matrix has the form of beads, flat sheet membrane or hollow fiber membrane.

6. The separation material according to claim 5, wherein the matrix has the form of flat sheet membrane or hollow fiber membrane and wherein the flat sheet membrane or hollow fiber membrane is treated with gas plasma before coupling a linker and a saccharide.

7. The separation material according to claim 1 wherein the saccharide is a mono-, di-, tri- or oligosaccharide which is able to bind to another molecule, protein or cell.

8. The separation material according to claim 7, wherein the saccharide is a blood group A determinant or/and a blood group B determinant.

9. A method for selectively separating substances having the ability to bind to saccharides from a liquid using a separation material according to claim 1.

10. The method according to claim 9, wherein the liquid is whole blood or a blood product.

* * * * *